US011540766B2

(12) United States Patent
Prado

(10) Patent No.: US 11,540,766 B2
(45) Date of Patent: Jan. 3, 2023

(54) NUCLEAR MAGNETIC RESONANCE SYSTEMS AND METHODS FOR NONINVASIVE AND IN-VIVO MEASUREMENTS USING A UNILATERAL MAGNET

(71) Applicant: Livivos Inc., San Diego, CA (US)

(72) Inventor: Pablo Jose Prado, San Diego, CA (US)

(73) Assignee: Livivos Inc., San Diego, CA (US)

( * ) Notice: Subject to any disclaimer, the term of this patent is extended or adjusted under 35 U.S.C. 154(b) by 588 days.

(21) Appl. No.: 16/178,317

(22) Filed: Nov. 1, 2018

(65) Prior Publication Data
US 2019/0076080 A1     Mar. 14, 2019

Related U.S. Application Data

(63) Continuation of application No. 15/868,996, filed on Jan. 11, 2018.
(Continued)

(51) Int. Cl.
*G01R 33/46* (2006.01)
*A61B 5/00* (2006.01)
(Continued)

(52) U.S. Cl.
CPC ............ *A61B 5/4244* (2013.01); *A61B 5/055* (2013.01); *A61B 5/4872* (2013.01);
(Continued)

(58) Field of Classification Search
CPC ..... A61B 5/4244; A61B 5/055; A61B 5/4872; G01R 33/383; G01R 33/3802; G01R 33/3808; G01R 33/4828; G01R 33/46
See application file for complete search history.

(56) References Cited

U.S. PATENT DOCUMENTS 5,172,060 A  * 12/1992  Knuttel .............. G01R 33/4833
                                                      324/300
5,744,960 A      4/1998  Pulyer
(Continued)

FOREIGN PATENT DOCUMENTS

EP        0900388 B1      7/2009

OTHER PUBLICATIONS

Philips, "3.0T Liver Transducer User Instructions and Special Safety References", 2010 (Year: 2010).*
(Continued)

*Primary Examiner* — Luther Behringer
*Assistant Examiner* — Adil Partap S Virk

(57) ABSTRACT

An apparatus for non-invasive evaluations and in-vivo diagnostics includes an open magnet, an RF antenna, and an NMR analytics logical circuit communicatively coupled to the RF antenna, wherein the open magnet is shaped to generate a static magnetic field that extends unilaterally into an object or internal organ of a subject when the open magnet is positioned against or in proximity to the object or subject, the static and RF magnetic fields shaped to generate a sensitive volume within a target region. The RF antenna or antenna array is configured to transmit RF pulses into the target region of the object or internal organ and receive sets of NMR signals generated by hydrogen or other elements, and the NMR analytics logical circuit is configured to obtain and analyze sets of NMR signals.

28 Claims, 14 Drawing Sheets

Related U.S. Application Data

(60) Provisional application No. 62/456,164, filed on Feb. 8, 2017, provisional application No. 62/720,300, filed on Aug. 21, 2018, provisional application No. 62/720,349, filed on Aug. 21, 2018.

(51) Int. Cl.
  *A61B 5/055* (2006.01)
  *G01R 33/38* (2006.01)
  *G01R 33/48* (2006.01)
  *G01R 33/383* (2006.01)

(52) U.S. Cl.
  CPC ..... *G01R 33/3802* (2013.01); *G01R 33/3808* (2013.01); *G01R 33/46* (2013.01); *G01R 33/4828* (2013.01); *G01R 33/383* (2013.01)

(56) References Cited

U.S. PATENT DOCUMENTS

| | | | |
|---|---|---|---|
| 5,855,555 | A | 1/1999 | Crowely |
| 5,959,454 | A | 9/1999 | Westphal et al. |
| 6,489,767 | B1 | 12/2002 | Prado et al. |
| 6,570,382 | B1 | 5/2003 | Hurlimann et al. |
| 6,977,503 | B2 | 12/2005 | Prado |
| 7,271,589 | B2 | 9/2007 | Melzi et al. |
| 7,358,734 | B2 | 4/2008 | Blumich et al. |
| 7,388,374 | B2 | 6/2008 | Minh et al. |
| 2001/0039377 | A1* | 11/2001 | Maier ............ G01R 33/56 600/410 |
| 2004/0158144 | A1 | 8/2004 | Karen |
| 2006/0084861 | A1 | 4/2006 | Blank |
| 2010/0260397 | A1* | 10/2010 | Block ............ G01R 33/5614 382/131 |
| 2012/0194193 | A1* | 8/2012 | Rehwald ........ G01R 33/4828 324/318 |
| 2012/0223705 | A1 | 9/2012 | Lowery |
| 2013/0088226 | A1* | 4/2013 | Miyazaki ....... G01R 33/5607 324/309 |
| 2014/0232403 | A1* | 8/2014 | Perkins ............ A61B 5/055 324/309 |
| 2014/0296697 | A1* | 10/2014 | Fenchel ........... G01R 33/481 600/411 |
| 2015/0301132 | A1 | 10/2015 | Wirtz |
| 2015/0341812 | A1 | 11/2015 | Dion |
| 2017/0227620 | A1* | 8/2017 | Wakai ............ A61B 5/0044 |
| 2017/0276747 | A1* | 9/2017 | Hugon ............ G01R 33/3873 |
| 2018/0184973 | A1 | 7/2018 | Nayak |
| 2018/0220949 | A1 | 8/2018 | Prado |

OTHER PUBLICATIONS

Dimitri Raptis et al., "MRI: the new reference standard in quantifying hepatic steatosis?", Oct. 13, 2011 (Year: 2011).*
Simon Graham et al., "Criteria for Analysis of Multicomponent Tissue T2 Relaxation Data", 1996 (Year: 1996).*
Scott Reeder et al., "Quantitative Assessment of Liver Fat with Magnetic Resonance Imaging and Spectroscopy", 2011 (Year: 2011 ).*
Sean Deoni et al., "Investigating White Matter Development in Infancy and Early Childhood Using Myelin Water Faction and Relaxation Time Mapping", NeuroImage, Aug. 2, 2012 (Year: 2012).*
Shao et al., "Resolving Multi-Component Overlapping GC-MS Signals by Immune Algorithms", 2009, Trends in Analytical Chemistry, vol. 28, No. 11 (Year: 2009).*
Deoni, "Magnetic Resonance Relaxation and Quantitative Measurement in the Brain", 2011, Magnetic Resonance Neuroimaging, pp. 65-108 (Year: 2011).*

Philips, "3.0T Liver Transducer User Instructions and Special Safety References," 2010.
Agopian et al., "Liver transplantation for nonalcoholic steatohepatitis: the new epidemic," Ann Surg. 2012; 256: 624-33.
Charlton et al., "Frequency and outcomes of liver transplantation for nonalcoholic steatohepatitis in the United States," Gastroenterology, 2011; 141: 1249-53.
Cippa et al., "Esitmating iron overlaod in patients wuith suspected liver disease and elevated serum ferritin," Am J Med. Oct. 2014.; 127(10): 1011.e1-3.
Demas et al., "Compact magnets for magnetic resonance," AIP Conference Proceedings, 2008, p. 36-9.
Eidmann et al., "The NMR Mouse, a Mobile Unviersal Surface Explorer," J. Mag. Reson., Series A, 104, 122.
Elmsjo et al., "NMR-based metabolic profilig in healthy individuals overfed different types of fat: links to changes in liver fat accumulation and lean tissue mass," Nutrition & Diabetes, 2015, 1.
Hu et al., "Change in the proton T(1) of fata and water in mixture," Magn Reson Med. Nov. 12, 2009.
Hussain et al., "Hepatic fat fraction: MR imaging for quantitative measurement and display-early experience," Radiaology Dec. 2005 237(3): 1048-1055.
Kamman, "Multi-exponential relaxation analysis with MR imaging and NMR spectroscopy using fat-water systems," Magnetic Resonance Imagingm, vol. 5, Issue 5, 1987, pp. 381-392.
Kleinberg et al., "Novel NMR Apparatus for Investigating an External Sample," J. Mag. Reson., 466, 97.
Lazo et al., "Prevalence of nonalcoholic fatty liver disease in the United States: The third national health and nutrition examination survey," 1988-1994. American Journal of Epidemiology. 2013. p. 38-45.
Lee et al., "Identifying metabolically obese but normal-weight (MONW) invidividuals in a nondiabetic Korean population: The Chungju Metabolic disease Cohort (CMC) study," Clin Endocrinal (Oxf.). 2011; 75:475-81.
Matzkanin, "A Review of Nondestructive Characterization of Composites Using NMR, in Non-destructive Characterization of Material," 1989, Springer, Berlin, 655.
Prado et al., "NMR Hand-Held Moistuer Sensor," 2001, Mag. Reson. Imaging, 19, 506.
Reeder et al, "Quantitative assessment of liver fat with magnetic resonance imaging and spectroscopy," J. Magn Reson Imaging, Oct. 2011; 34(4): 729-49.
Reeder et al, "Proton density fat-fraction: a standardized MR-based biomarker of tissue fat concentration," J Magn Reson Imaging, Nov. 36, 2012;36(5): 1011-4.
Renou, "Use of low resolution NMR for determining fat content in meat products," Journal of Food Technology, 1985, 20, 23-29.
St. Pierre et al., "Noninvasive measurement and imaging of liver iron concentrations using proton magnetic resonance," Blood 2005, 105 855-61.
Vernon, "Systematic review: the epidemiology and natural history of non-alcoholic fatty liver disease and non-alcoholic steatohepatitis in adults," Aliment Pharmacol Ther. 211; 34: 274-85.
Wildman et al., "The ovese without cardiometabolic risk factor clust4ering and the noral weight with cardiometabolic risk factor clustering: prevalence and correlates of 2 phenotypes among the US population (NHANES 1999-2004)," aRCinTERN Med., 2008; 168: 1617-24.
Williams et al., "Prevalence of nonalcoholic fatty liver disease and nonalcoholic steatohepatitis among a largely middle-aged population utilizing ultrasound and liver biopsy: A prospective study." Gastroenterology, 2011; 140: 124-31.
International Search Report and Written Opinion in PCT/US19/ 47577, dated Nov. 13, 2019.
International Preliminary Report on Patentability in PCT/US2019/ 047577, dated Feb. 23, 2021.

* cited by examiner

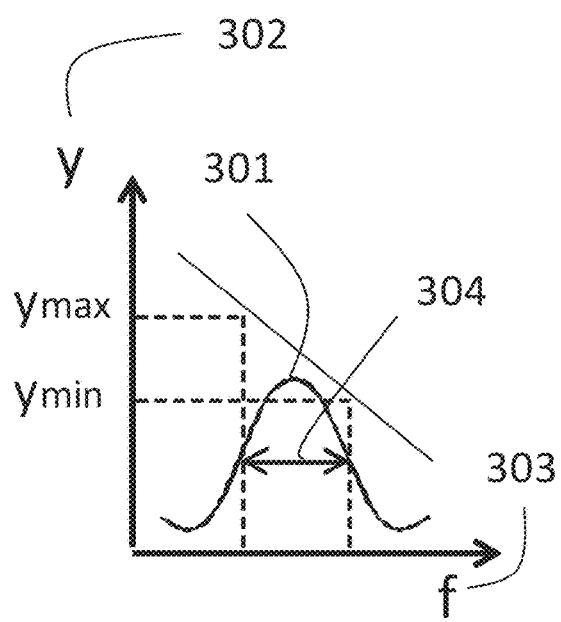
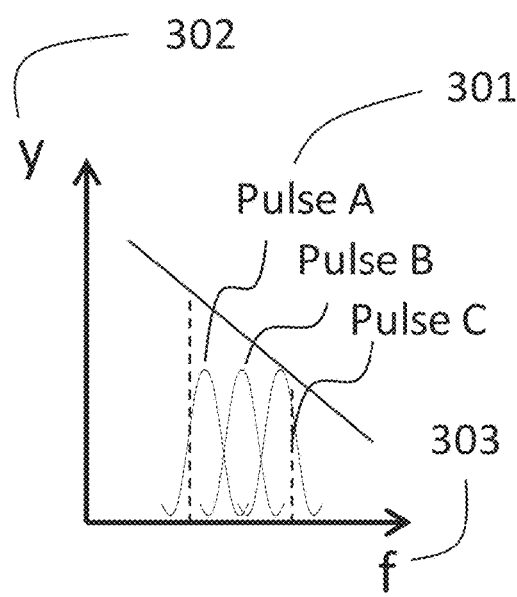
FIG. 3A　　　　FIG. 3B

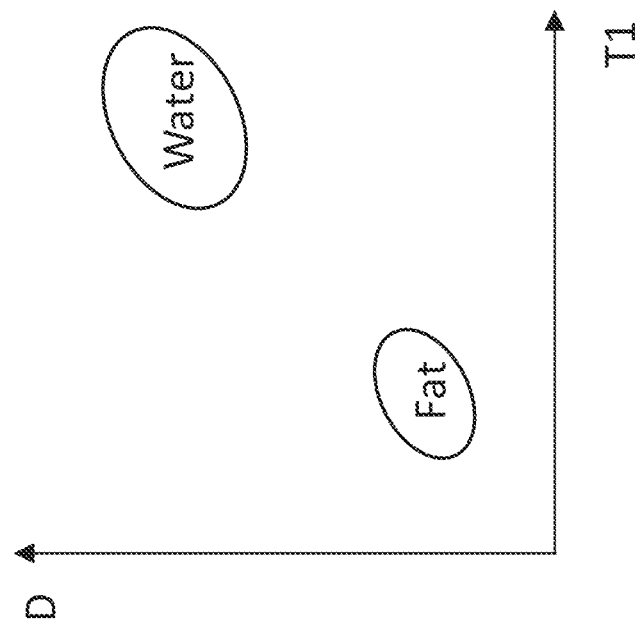
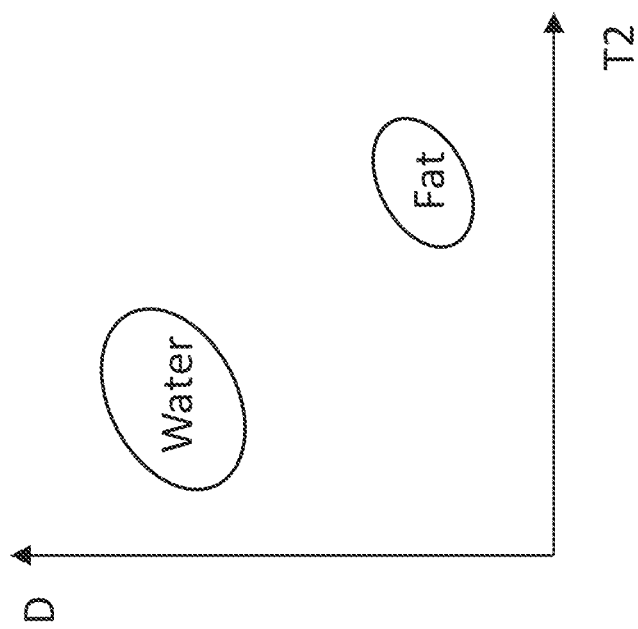
Fig. 14

NUCLEAR MAGNETIC RESONANCE SYSTEMS AND METHODS FOR NONINVASIVE AND IN-VIVO MEASUREMENTS USING A UNILATERAL MAGNET

CROSS-REFERENCE TO RELATED APPLICATIONS

This application is a continuation of and claims priority to U.S. patent application Ser. No. 15/868,996, filed Jan. 11, 2018, which claims priority to U.S. Provisional Application No. 62/456,164, filed Feb. 8, 2017. The present application also claims priority to U.S. Provisional Patent Application No. 62/720,300 filed Aug. 21, 2018, and U.S. Provisional Application No. 67/720,349, filed Aug. 21, 2018, the contents of which are incorporated herein by reference.

FIELD

The present disclosure generally relates to medical devices. More particularly, the present disclosure relates to compact Nuclear Magnetic Resonance ("NMR") systems and methods for in-vivo and non-invasive measurements of properties of a human or animal body using a unilateral magnet.

BACKGROUND

Clinical Magnetic Resonance Imaging (MRI) is a mature medical imaging technology used for a number of diagnostic procedures. Typically, MRI systems are configured to use cylindrical or C-shaped magnets (i.e., a magnetized enclosure) to create a magnetic field within the enclosure to which Hydrogen atoms line up their nuclear spins. The MRI system may then use a radio frequency (RF) to effectively knock the spinning Hydrogen atoms off their polarization axis, and then detect a radio frequency signal generated by the Hydrogen atoms returning back to their aligned spin position with the magnetic field. Using this technique and controlled space-varying magnetic fields, an MRI can scan a human or animal body in three-dimensions to create an internal image of the subject, which varies in contrast based on Hydrogen content and the characteristics of the tissue surrounding the Hydrogen atoms. MRI can also be used to directly or indirectly measure relative quantities of other elements apart from Hydrogen, e.g., Sodium and Iron. MRI can also be used to quantify the relative amount of Hydrogen in certain molecules of tissues, e.g. Hydrogen in fat, tissues or water.

MRI magnets tend to be large and expensive, and must be housed in specialized facilities with non-standard power and specialized shielding to accommodate the super-cooled magnetic coils and large magnetic fields. The excessive cost and the demand for dedicated facilities makes MRI prohibitive for the majority of preventive medicine procedures, therapeutic efficacy evaluation and periodic checkups. Accordingly, while MRI may be used to facilitate diagnostic and screening procedures aimed at measuring particular target substances within human or animal organs, e.g., liver fat, iron, sodium, etc., the technology is costly, inefficient, and not universally accessible. Other modalities, such as ultrasound, may also be used at a lower cost to measure properties of the target substances, but those modalities tend to be less accurate, specific, and/or reliable than MRI.

With the significant increase in metabolic syndrome incidence, it has become important for internal medicine and specialist practitioners to be able discriminate patients at highest risk for severe complications, such as type II diabetes and liver cirrhosis. These trends suggest the need for tools for safe, non-invasive, and inexpensive assessment of, for example, liver disease. Also, it points to the advantages of performing periodic and accurate monitoring of clinical treatments.

Of particular interest is liver disease diagnostics. Non-alcoholic fatty liver disease (NAFLD) is the most common hepatic disorder in the United States. Some patients with NAFLD develop non-alcoholic steatohepatitis (NASH, abnormal retention of lipids), leading to cirrhosis, and the eventual need for a liver transplant. Further, a large number of patients with normal weight suffer from multiple aspects of metabolic syndrome, including NAFLD and NASH. Disease recognition is often delayed in these patients, relative to obese patients, leading to more severe complications. Also, since sarcopenia and fatty replacement is a key finding of metabolically obese normal-weight (MONW) subjects, a useful application is tracking fat concentration in limb musculature.

Assessment of hepatic steatosis for clinical care requires diagnosis and grading of severity. The relevant classification threshold may vary, from the standard 5% steatosis threshold defining hepatic steatosis, to a 30% threshold for sometimes used to exclude liver transplantation donors. Accurate quantification is helpful for grading steatosis and for longitudinal monitoring of patients.

If accurate and low cost diagnostics are readily available for quantifying fat content, early indicators could lead to a significantly reduction of the incidence of liver disease.

Additionally, iron overload occurs in liver disease, metabolic syndrome and hereditary hemochromatosis, in hemodialysis patients receiving supplemental iron, and in patients who receive multiple red-cell transfusions for thalassemia, sickle-cell disease (SCD), and myelodysplastic syndrome (MDS). Iron overload can cause death from heart failure, liver cancer, or cirrhosis, as well as diabetes, endocrine deficiency and joint problems. It may increase risks of hepatocellular cancer in alcoholic liver disease (ALD) and NASH, exacerbate fibrosis in ALD, affect insulin resistance and liver dysfunction in some patients with metabolic syndrome, and contribute to immune dysfunction and heart failure in hemodialysis. Together, these conditions affect millions of patients.

Traditional methods used to quantify iron overload are ambiguous, invasive, or expensive. Typically, clinicians infer iron status from serum ferritin and transferrin saturation. However, these indicators are inherently ambiguous, because they are affected by liver disease, inflammation, hemolysis and other common conditions. As a result, diagnosing iron overload can be a complicated process that may include genetic tests for hemochromatosis, and integrating multiple clinical signs and serum tests to rule out inflammation, liver disease and other confounding factors. Liver iron measurements by biopsy or MRI are more direct and less ambiguous, but liver biopsy is invasive, while an MRI scan is expensive and not readily available in all locations.

BRIEF SUMMARY OF EMBODIMENTS

A low cost, compact Nuclear Magnetic Resonance (NMR) instrument examining specific volumes in the body provides valuable and quality data comparable to data generated by MRI, but at the cost of simpler portable clinical instruments such as ultrasound machines.

Embodiments of the disclosed technology provide a compact flat, tapered, or curved unilateral probe to inspect human or animal organs in-vivo and non-invasively. In the context of the present disclosure, "unilateral" NMR probe means that the probe is open. There is no need to fully enclose the sensitive volume with the scanning probe, as is the case with conventional MRI magnets. The scanning probe is placed in the proximity of the body or on the body. The probe may generate a sensitive volume outside or inside of the boundaries of the probe, as explained hereafter. Other terms sometimes used to describe unilateral NMR probes may be, for example, "single sided" and "open." The term "single sided" may be used to refer to magnets that generate sensitive volumes only outside of the boundaries of the magnet. For clarification, in the present disclosure, the sensitive volume may be beyond or within the outer boundaries of the scanning probe.

A unilateral NMR configuration enables a number of diagnostic procedures without utilizing large and expensive MRI devices. Of special attention is the capability to inspect the liver, but other organs and parts of the body may also be inspected with the open NMR probe. This probe need not generate an image, but merely measures properties of selected volumes of organs inside of the human or animal body. Spatial resolution (imaging) may be achieved by frequency or phase encoding methods. Given the inhomogeneity of the fields generated by open magnets, the sensitive volume is somewhat limited and therefore imaging is of interest when inspecting smaller features in the body. Applications such as fat or iron in the liver or sodium in skin or muscle do not require imaging, rather performing NMR measurements in a selected volume is sufficient.

The disclosed technology utilizes NMR properties of elements such as proton and sodium to address specific clinical applications. In some examples, the disclosed technology may be used to quantify the level of fat in liver or the level of sodium in tissue or blood. Of special interest is the diagnosis of liver disease based on the correlation to, for example, hepatic fat content.

The present disclosure provides an NMR apparatus with a compact probe that may be flat, tapered, or curved and may be positioned on or in proximity to a subject's body. The subject may be human or animal. The compact probe may be portable or have a relatively small footprint when compared with commercial MRI scanners. The compact probe is also generally lower cost, consumes less power, and creates a lower magnetic field than commercial MRI scanners. The NMR apparatus disclosed herein may generate MRI-type data for a number of unmet medical needs. For example, a small clinic could perform non-invasive liver examinations in minutes or seconds with an economical device with the accuracy and reliability of, e.g., an MRI system, but the footprint, portability, and relatively low cost of an ultrasound instrument.

As an example, liver fat and iron content may be measured accurately using NMR and MRI methods. With traditional MRI methods, the liver fat and iron contents are measured by analyzing the signals from selected pixels in the liver and the distinctive response of protons in fat, water and tissues. With NMR spectroscopy and MRI spectroscopy (MRIS), the signals from protons in fat may be discriminated from signals from surrounding water and tissue based on the proton NMR spectrum. In the human and animal bodies, protons are abundant in water, in fat (triglycerides), and in other tissues. Protons may be part of fat or water molecules and be bond to tissues or mobile ("free").

Tissue fat comprises long carbon-chain triglycerides. Each triglyceride molecule contains protons in different chemical environments. Neighboring nuclei in the long chains generally interact with each other through a distortion of their electron clouds in a process known as J-coupling. This J-coupling is detectable and recognizable in NMR signals, e.g., in response to disturbing the spin axes of J-coupled protons relative to a magnetic field using different RF pulse frequencies. This is important for NMR-based chemical analysis because it enables differentiation of fat based on shifts in the spectral lines resulting from the J-coupling effect.

NMR signals may also be attained with unilateral probes, in which the sensitive volume is either inside or outside of the scanner. Unilateral NMR probes, and particularly low-magnetic field unilateral NMR probes, typically generate non-uniform magnetic fields which are not conducive to MRIS methods.

Embodiments of the present disclosure are directed to unilateral NMR systems that use low spectral resolution NMR techniques and a pseudo-spectroscopic fat quantification method in order to accommodate the non-uniform magnetic field generated by the unilateral NMR probe. Using multi-pulse echo train techniques, spectroscopic differentiation may be achieved indirectly based on the specific timing of NMR multi-pulse sequences, even in the presence of non-uniform magnetic fields.

In some examples, the unilateral probe includes a unilateral magnet with a proximal surface and a distal surface, the distal surface being shaped with a negative curvature and/or taper in order to enclose an empty space or cavity within the magnet's profile. The magnet may be positioned with the distal surface against or in proximity to a subject's body as to partially enclose the subject's body, and a selected internal organ and/or region of interest, within the empty space inside the negative curvature of the magnet. By shaping the magnet this way, the magnetic field may be better controlled on a sensitive volume within the target region, resulting in high efficacy in a unilateral NMR measurement.

With low spectral resolution NMR instruments, the relative concentration of fat may be based on multi-component relaxation and diffusion parameters attained from analysis of the NMR signals. Identifying and quantifying iron with NMR signals may be accomplished based on the effect on relaxation times of the proton NMR signal. Iron detection and quantification may further be facilitated using multiple magnetic field strengths. A correlative relationship between iron content and NMR measurements at varying magnetic field strengths may be generated empirically using historical MRI and/or NMR data.

Open NMR probes provide the capability of analyzing objects that are larger than the probe itself. An example is a broadly-used borehole NMR probe that measures signals from water and oil in the formations surrounding the probe. In some embodiments of the present disclosure, a compact unilateral probe may project a magnetic field, e.g., inside a human or animal bodies, and organs contained therein, without having to enclose or otherwise completely surround the subject with the magnet. In other words, a unilateral NMR probe, as disclosed herein, may collect NMR signals from inside the body by simple placing a flat, tapered, or curved probe in the proximity of the organ or region to be examined.

As an example, clinically relevant indicators such as fat or iron content in the liver may be determined by measurable NMR parameters. The open probe can identify and quantify fat, iron, sodium or other substances in several volumes of the organs and skeletal muscle. Embodiments of the disclosed technology may be applied to reliably and accurately detect and monitor health issues related to iron and/or fat content in the liver and other organs at a low cost relative to MRI, generating accurate clinically-relevant measurements. Measurements of the fat or iron content may be based on singling out proton NMR signals based on their characteristics such as relaxation times and spectral shifts. The diffusion parameters may also be used as a discrimination factor between the protons in fat or water and surrounding tissues. Methods disclosed herein may also be used to compute the relative and absolute content of fat and iron in human and animal organs.

For example, by providing a simultaneous readout of iron concentration and fat fraction, a practitioner can discriminate hyperferritinemia from metabolic syndrome from true iron overload.

In one aspect of the present disclosure, an apparatus for measuring liver fat or iron content, or sodium or phosphorous content in muscle tissue non-invasively and in-vivo using a unilateral NMR probe is disclosed. The NMR probe may include a flat, tapered, curved, or other shaped magnet. In some embodiments, the NMR probe may include multiple magnets affixed or located in proximity to each other to generate the desired magnetic field shape. The magnet(s) may be permanent or electro-magnetic in nature.

The disclosed apparatus may include a probe positioned against or in the proximity to the body. The probe may generate a sensitive volume inside the body. The apparatus may also include an RF antenna placed between a magnet and the body or around the magnet. The antenna may be used to attain NMR signals. The probe may generate static and RF magnetic fields used to cause NMR response signals from selected regions and depths within a subject's body. The resulting NMR signals may be stored, processed, and measured to determine characteristics of the selected regions and depth, e.g., fat and iron content within the specific volume or at various regions inside the liver or sodium or phosphorous content in muscle tissue. The measurement may be performed at a number of selected specific volumes with or without repositioning the probe. This could be used to determine the fat, iron, sodium or phosphorous content at various positions in the organ of interest or to generate a profile.

The iron content may be determined indirectly, by the effect of iron in the proton NMR relaxation time, which may be detected in the NMR response signal.

It should be noted that the NMR methods and systems disclosed herein, although described with reference to their applications for detecting iron or fat in the liver and sodium or phosphorous in muscles, may also be applied to other elements and other internal and/or external organs, e.g., the heart, lungs, brain, esophagus, salivary glands, mouth, pharynx, larynx, stomach, pancreas, bladder, intestines, kidneys, gallbladder, spleen, skeleton, blood, blood marrow, arteries, veins, lymph nodes, reproductive organs, and/or other internal and/or external organs in humans and/or animals. The NMR methods and systems disclosed herein may also be applied to the detection and quantifications of other spectrographically discernable substances apart from iron and fat, e.g., proteins, nucleic acids, carbohydrates, hydrocarbons, potassium, phosphorous, sodium, copper, and/or other metals, elements, and organic or non-organic molecules.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention.

FIG. 3A is a chart illustrating an example relationship between RF frequency and distance from the unilateral NMR antenna for an example RF excitation and response signal, consistent with embodiments disclosed herein.

FIG. 3B is a chart illustrating example relationships between RF pulse bandwidth and distance from the unilateral NMR antenna for example RF excitation and response signals at three different frequencies, consistent with embodiments disclosed herein.

FIG. 14 shows examples of 2-dimensional distribution plots of T2 relaxation times and diffusion parameters and T1 recovery times and diffusion parameters, respectively.

Figure 1A:
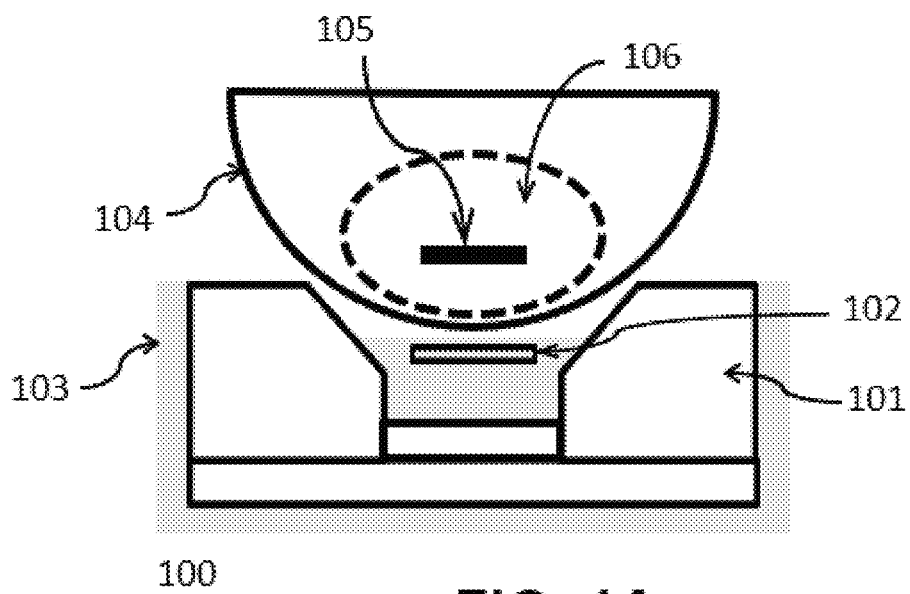
FIG. 1A is a schematic diagram illustrating a cross-section view of an example unilateral NMR apparatus for in-vivo diagnostics, in accordance with embodiments disclosed herein, with the sensitive volume outside of the boundaries of the apparatus.

These figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS

The present disclosure is directed towards systems and methods for non-invasive and in-vivo measurement of characteristics of a subject's organ using a unilateral NMR apparatus. The subject may be human or animal. The target organ may be a liver, heart, lungs, brain, esophagus, salivary glands, mouth, pharynx, larynx, stomach, pancreas, bladder, intestines, kidneys, gallbladder, spleen, skeleton, muscles, blood, blood marrow, arteries, veins, lymph nodes, reproductive organs, and/or other internal and/or external organs in humans and/or animals. The element analyzed by NMR may be hydrogen (conventional proton NMR), sodium, phosphorous, or other elements directly or indirectly observed by NMR.

In some embodiments, a medical apparatus for non-invasive and in-vivo examination of an internal organ (e.g., a liver or muscle) includes a unilateral magnet, an RF antenna mechanically coupled to the magnet, and an NMR analytics logical circuit communicatively coupled to the RF antenna. The magnet and RF antenna together may constitute an NMR probe. The analytics logical circuit may include a processor and a non-transitory computer readable medium with computer executable instructions embedded thereon, wherein the computer executable instructions are configured to cause the processor to perform methods and processes as disclosed herein.

In some embodiments, the magnet is shaped to generate a magnetic field that extends unilaterally into an internal organ of a subject when the magnet is positioned against or in proximity to the subject, the magnetic field shaped to generate a sensitive volume within a target region of the internal organ. For example, the magnet may be flat, tapered, or curved. The magnet may comprise multiple magnetic components affixed together or positioned in proximity to each other to generate the desired magnetic field strength and distribution. The magnet may be a permanent magnet, an electromagnet, or a combination of permanent magnet and an electromagnet. The compact magnet may be hand portable or mechanically coupled to, e.g., a pedestal, cart, table, or retractable arm.

In some examples, the RF antenna may be configured to transmit RF pulses into the target region of the internal organ that disturbs the spin axes of protons or other nuclei inside the target region. For example, the RF antenna may include an RF control logical circuit configured to control power to the RF antenna to cause the antenna to transmit desired RF frequency pulses. The RF control logical circuit may be communicatively coupled to an NMR probe analytical circuit, which may be configured to obtain user input (e.g., from a graphical user interface or GUI), display NMR data on the GUI, and control the RF antenna per user instructions and preconfigured parameters.

In some examples, the RF antenna and/or RF control logical circuit may be configured to receive a set of NMR signals. For example, an NMR signal may be generated by a nucleus of an atom as its axis of spin is disturbed by an RF pulse, and then realigns to a magnetic field.

In some embodiments the NMR analytics logical circuit may be configured to obtain the set of NMR signals (e.g., a first set and a second set of NMR signals). The NMR analytics logical circuit may further be configured to identify a first signal amplitude, a first T2 relaxation time, a first T1 recovery time, and/or a first diffusion parameter corresponding to the first set of NMR signals. In some examples, the NMR analytics logical circuit may be configured to identify a second signal amplitude, a second T2 relaxation time, a second T1 recovery time, and/or a second diffusion parameter corresponding to the second set of NMR signals and differentiate a first substance type corresponding to the first set of NMR signals from a second substance type corresponding to the second set of NMR signals based on distinguishing the first and second signal amplitudes, the first and second T2 relaxation times, the first and second T1 recovery times, and/or the first and second diffusion parameters.

In some embodiments, the NMR analytics logical circuit may be further configured to generate a J-coupling relationship between substance types (i.e., a first substance type and a second substance type present in the sensitive volume) based on a comparison of the first and second NMR signals, and further distinguish substance types based on the J-coupling relationship. The NMR analytics logical circuit may further configured to determine whether one of the substance type is fat based on the T2 relaxation times, the T1 recovery times, the diffusion parameter, and/or the J-coupling relationship. The NMR analytics logical circuit may be further configured to determine whether the substance type is iron based on the T2 relaxation times, the T1 recovery times, the diffusion parameter, and/or the J-coupling relationship.

In some embodiments, the RF antenna may include an open coil configured to transmit RF pulses in a substantially perpendicular orientation to the magnetic field. The RF antenna may further include an open coil array configured to transmit RF pulses in a substantially perpendicular orientation to the static magnetic field.

In some examples embodiments, the analytics logical circuit may be configured to quantify a fat concentration by applying a discrete multi-exponential signal decay model to the NMR signals.

The analytics logical circuit may be configured to plot, on the GUI, a 2-dimensional distribution of the T2 relaxation times and the diffusion parameters and/or a 2-dimensional distribution of the T1 recovery times and the diffusion parameters, as showing in FIG. 14. In some examples, the analytics logical circuit may be configured to determine a relative fat concentration based on a ratio of signal amplitudes from a multi-exponential decay analysis (e.g., by comparing the amplitude of the first set of NMR signals with the amplitude of the second set of NMR signals).

In other embodiments, the analytics logical circuit is further configured to obtain, from a NMR signal database, a calibration signal amplitude for liver fat and determine an absolute fat concentration based on the amplitude of the fat NMR signals as compared with the calibration signal amplitude. For example, the NMR signal database may include historical NMR signal data acquired from subjects with known liver fat quantities and/or phantoms. In some examples, the calibration signal amplitude may be determined by applying a machine learning model to a training data set, the training data set including multiple historical NMR signals acquired from multiple subjects and/or phantoms, and corresponding liver fat readings. The machine learning model may be a convolutional neural network (CNN), a logistical regression, a decision tree, or other machine learning algorithm.

Embodiments disclosed herein may be used to measure human and animal tissue properties for medical and veterinarian diagnostics but utilizes a compact, low cost diagnostic instrument with a probe placed against or near by the body, in the proximity of the organ to be assessed. Various diagnosis procedures may be based on dedicated NMR methods utilizing unilateral probes and exploiting the inherent magnetic field gradients present in open magnets.

Figure 1B:
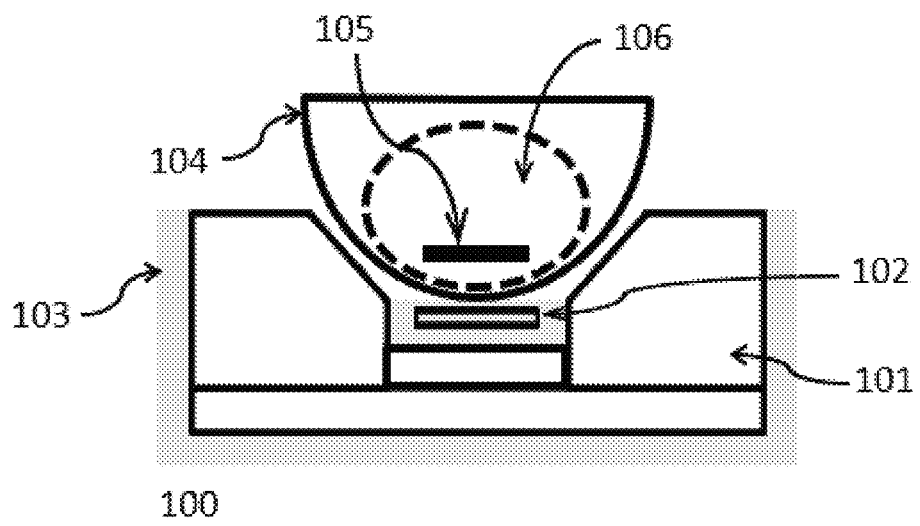
FIG. 1B is a schematic diagram illustrating a cross-section view of an example unilateral NMR apparatus for in-vivo diagnostics, in accordance with embodiments disclosed herein, with the sensitive volume inside of the boundaries of the apparatus.
Figure 1C:
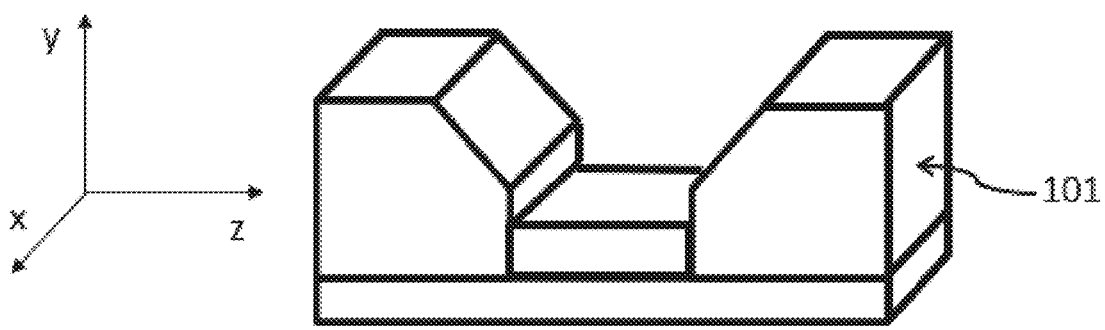
FIG. 1C is a schematic diagram illustrating a perspective view of an example unilateral NMR apparatus for in-vivo diagnostics, in accordance with embodiments disclosed herein.

FIGS. 1A and 1B are schematic diagrams illustrating an example open NMR apparatus for in-vivo diagnostics. Referring to FIGS. 1A, 1B, and 1C an apparatus for in-vivo diagnostics may include a permanent or electro magnet 101, an RF antenna 102, and a probe enclosure 103. The figures further illustrate a body of a patient 104, a sensitive volume 105, and an organ being examined 106. The magnet array may have an open and long geometry, to accommodate placing the probe on the body or in the proximity of the body of a patient or animal. This geometry may be used to follow a patient or animal body contour, facilitating observing organs shallow or deep into the body.

The apparatus 100 may be placed on or near the patient, for example in the proximity of the organ of interest (e.g., a liver, heart, lungs, brain, esophagus, salivary glands, mouth, pharynx, larynx, stomach, pancreas, bladder, intestines, kidneys, gallbladder, spleen, skeleton, muscles, blood, blood marrow, arteries, veins, lymph nodes, reproductive organs, and/or other internal and/or external organs). Positioning the device may be aided by an ultrasound device, estimating the patient's distance between the skin and the organ being examined. Once the distance is determined, the unilateral probe is positioned in the proximity of the organ being examined and at a distance from the body that ensure the sensitive volume is inside the organ if interest. The position of the sensitive volume may also be controlled by changing the NMR frequency. Positioning may also be done by performing preliminary NMR measurements observing the various tissues, generating a profile or directly-focusing the reading at a point deep into the body based on knowledge of the expected position of the organ.

The apparatus may use a unilateral NMR probe 100 abutted against the body of a patient, as shown in FIGS. 1A and B. In some examples, the NMR probe 100 may be positioned in proximity to, but not abutted against the body of the patient. The unilateral magnet 101 generates a static magnetic field that may be produced by a controlled-current electromagnet, by a permanent magnet array, or by a combination of the two. The apparatus 100 may include an RF antenna 102, wherein the RF antenna may include RF transmitter and receiver coils. In some examples, the RF antenna may also include an RF control logical circuit. For example, the RF control logical circuit may include a processor and a non-transitory medium with computer executable instructions embedded thereon, the computer executable instructions configured to cause the RF transmitter coils to transit RF frequency pulses in accordance with pre-determined and/or user selected protocols.

An RF field may be produced by the RF antenna in a substantially perpendicular direction relative to the static magnetic field generated by the permanent or electro-magnet. In some examples, the RF antenna may include multiple subcomponent RF elements, e.g., an RF antenna array. The transmit and receive coils of the RF antenna may be separate elements or a combined transmit-receive element. The unilateral permanent magnet and the RF antenna may be configured to project safe magnetic fields into a subject's body.

In some embodiments, the unilateral magnet may generate a non-uniform magnetic field. The non-uniform magnetic field distribution may be used to achieve spatial selectivity and to measure diffusion parameters. Diffusion parameters help discriminates between the various tissues and water present in a selected volume inside the human or animal body. The field distribution may also be controlled using controlled current gradient coils or using shimming magnet or ferrous elements. The shape of the magnet blocks, their magnetization level and direction, shimming elements and gradient coils all play a role in the control of the static magnetic field of the unilateral probe.

Field variations in the magnetic field may be established within the sensitive volume, e.g., by varying the field generated by a unilateral electromagnet or by repositioning a permanent or electro magnet. Additionally, measurements at more than one field may be achieved by selecting more than one volume (i.e., a different magnetic field within the inhomogeneous magnetic field) and assuming a low variability in iron content between the selected volumes.

For purposes of the present disclosure, the volume within which meaningful results may be produced is referred to as the sensitive volume 105. Proton and/or other atomic nuclei spin axes within the sensitive volume will tend to align with magnetic field, i.e., line up parallel to the field direction or polarize. The atomic nuclei (e.g., Hydrogen's proton) spin alignment may be permuted by exciting the atomic nuclei with one or a series of RF pulses generated by the RF transmitter. In other words, the spinning nuclei are "knocked off" of their preferred spin axis in relation to the static magnetic field. The RF pulses are delivered via the RF antenna 102. As the excited atomic nuclei realign to the external magnetic field, they emit RF signals (also referred to herein as NMR signals) that may be detected by the RF receiver within the RF antenna or connected to the RF antenna 102. The RF receiver antenna may be the same RF transmitter antenna 102 or a separate element. The frequency of the NMR signal will be proportional to the strength of the external magnetic field. The signal lifetime depends on properties such as the mobility of the nucleus and the composition of its surrounding tissue.

In unilateral NMR, the magnet has an open configuration, such that NMR signals are generated from a region removed from the probe 100 or within the probe.

The unilateral magnet in the NMR probe disclosed herein may be flat, tapered, or curved, permitting access from one side of the body, in the proximity of the organ of interest. In some examples, the NMR signal may be obtained with a RF antenna positioned between the magnet and the patient (as shown in FIGS. 1A and B). In other examples, the RF antenna may be positioned adjacent to or otherwise near the magnet. The positioning of the sensitive volume will be determined by the distribution of the static and the RF magnetic fields generated by the magnet and RF antenna and by the frequency of the excitation pulses.

Figure 2A:
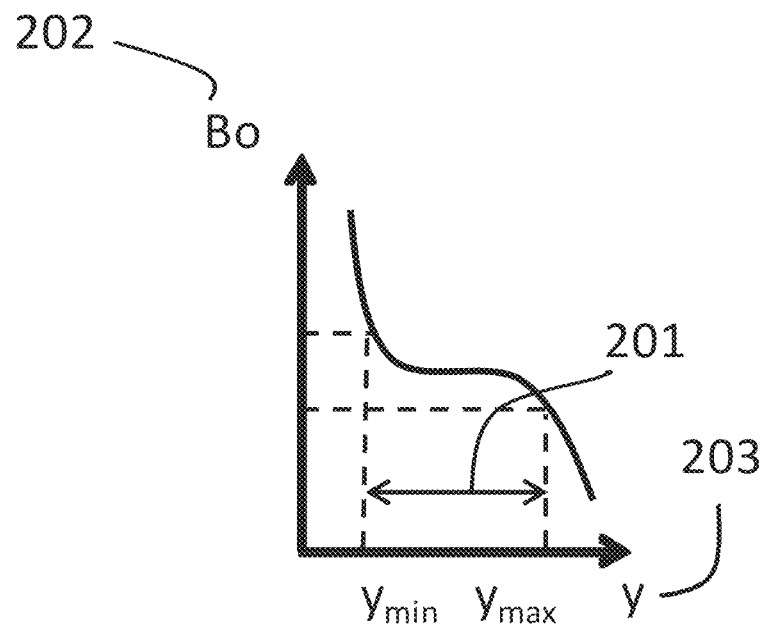
FIG. 2A is a chart illustrating an example distribution of magnetic field amplitude along a y-axis for a unilateral NMR probe, extending out in the y-direction outward from the NMR probe, consistent with embodiments disclosed herein.
Figure 2B:
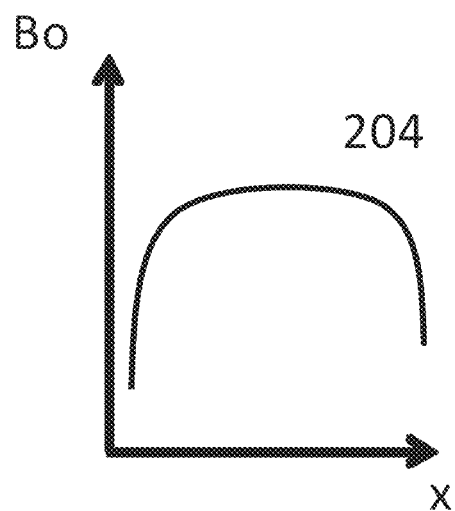
FIG. 2B is a chart illustrating an example distribution of magnetic field amplitude along the x-axis for a unilateral NMR probe, extending along the x-direction in the NMR probe, consistent with embodiments disclosed herein.

FIG. 2A is a chart illustrating an example distribution of magnetic field amplitude or magnitude along a y-axis for a unilateral NMR probe, extending out in the y-direction from the NMR probe. FIG. 2B is a chart illustrating an example distribution of magnetic field amplitude extending along the x-direction in the NMR probe, for example along or across the gap in the magnet array shown in FIG. 1. Referring to FIGS. 2A and 2B, the size of the sensitive volume may be determined by the bandwidth of the RF pulses and the magnetic field distribution. As can be seen in FIG. 2A, an example of the magnetic field distribution for the unilateral NMR probe is shown. "y" represents the direction outwards from the magnet, into the body. Depth Range is indicated by numeral 201, Magnetic Field Amplitude is indicated by numeral 202, and Depth of Penetration is indicated by numeral 203. The depth range is determined based on the excitation frequency, which is proportional to the static magnetic field, the limited frequency bandwidth of the RF pulses, and the characteristic frequency response of the NMR sequences used. A frequency bandwidth translates into a static magnetic field range, which in turn translates into a physical extend. The broader the pulse bandwidth, the larger the excited region. Bandwidth may also be varied by the RF pulse modulation and by the pulse sequence timing in a multi-pulse NMR protocol.

In some embodiments, the NMR probe may include a magnet array. The configuration of the magnet array may be customized to generate an extended sensitive volume. This phenomenon can be observed in FIGS. 2A and 2B in the depth direction (y) and in the direction along the extruded direction of the flat or curved magnet (x). The extended range in any of the directions may be achieved by shimming the magnet. An inflexion point in the field distribution 202 may be generated by incorporating secondary magnets with opposite polarity to that of the primary magnet poles of the magnet array. This effectively subtracts magnetic field in the proximity of the secondary magnet. The effect is less pronounced at greater distances from the secondary magnets, where the main pole field is dominant. The secondary magnets may then be positioned in such way that an extended depth range is achieved.

In the direction along the magnet gap or well, an extended range may be achieved by making a longer primary magnet or by placing small gaps between the secondary magnets in order to modulate the shape of the field 204. In some examples, the primary and secondary magnets may be magnet blocks of various shapes, including cubes, rectangular prisms, triangular prisms, bars, cylinders, or trapezoidal prisms. Other shapes may be used for both the primary and secondary magnets to achieve the desired magnetic field distribution.

In some embodiments, the magnet may generate a magnetic field with a maximum strength ranging from about 0.03 to about 1.0 Tesla. In some examples, field strengths between about 0.05 and about 0.5 Tesla may be used, which correspond to about 2 MHz to about 20 MHz range of operation. As used herein, the term "about" may indicates that the recited values may vary by as much as 5%. In some examples, the magnet blocks forming the magnet array may include materials such as NdFeB or SmCo. Alloys based on SmCo may be used to build magnets with low temperature coefficient. Low temperature coefficient may be used to reduce field drift due to temperature changes, which may cause changes to the shape and/or position of the sensitive volume. The temperature affects may be accounted for by shifting the RF frequency, controlling the temperature of the magnet, or repositioning the probe if the shift is significant. The temperature coefficient of NdFeB permanent magnets is about 0.1%/C at room temperature. The temperature-driven field drift is smaller for SmCo.

To accommodate different organs, subject body sizes and ages, and other variations in the target sensitive volume, the NMR probe may be customized in size, shape, field strength, and other parameters for a specific depth of penetration and sensitive volume shape and size. For example, with a monotonically decreasing field, the deeper the examined region the lower the field and the frequency.

The extension and position of the sensitive volume may be changed by frequency encoding using a single, broadband excitation pulse or a series of pulses with different frequencies. FIG. 3A illustrates an excitation of a depth of interest with a single, broadband RF pulse. The frequency (f) dependency with depth (y) is determined by the distribution of the static magnetic field. FIG. 3B illustrates an excitation of the depth of interest with three RF pulses of slightly different frequency. The frequency (f) dependency with depth (y) is determined by the distribution of the static magnetic field change in sensitive volume. Numeral 301 indicate Frequency Response, Depth of Penetration is indicated by numeral 302, Frequency is indicated by numeral 303, and Bandwidth is indicated by numeral 304.

A stronger RF pulse with a shorter duration may be used to generate a larger sensitive volume range. In such examples, the RF antenna may be configured to accommodate broadband pulses, the RF pulse field strength may be on the order of about 1 Gauss, or 0.0001 Tesla, and the RF pulse durations may be on the order of about 5 microseconds to about 200 microseconds. The quality factor (Q) of the probe is a measure of the electromagnetic response bandwidth of a resonant circuit. A relatively low Q probe may be used for broad bandwidth pulses. A switching RF amplifier (e.g., H-bridge or Class D transmitters) may be used to accommodate short duration RF pulses, which are beneficial in inhomogeneous fields.

The he sensitive volume may be represented by the relationship $\Delta y \sim (2\pi/\gamma)$ $(tp\ \delta Bz/\delta y)^{-1}$, where tp is the RF pulse duration, z is the direction of the static magnetic field—across the probe head top—and y is the direction away from the probe. As the excited volumes become thinner, the effective filling factor of the probe decreases. This reduces the sensitivity during data acquisition.

The signal-to-noise-ratio (SNR) for an RF coil at temperature Tc, generating a $B_1$ RF field and with resistance rc may be represented by the relationship, $$SNR \frac{B_1/I}{\sqrt{rsTs + rcTc}} VM\sqrt{to},$$

where V is the excited volume, l is the current necessary to generate B1, rs and Ts are the sample resistance and temperature, respectively. M is the transverse magnetization at the observation time tc. As the coil diameter of an open loop antenna is decreased, the RF field per unit current increases approximately linearly and the sample resistance decreases as the power of three.

To control the location of the sensitive volume within the organ of interest, the NMR probe may be repositioned to alter the gap between the body and the probe, the RF frequency may be adjusted to excite a different region as the field is non-uniform and proportional to the frequency, and/or the magnetic field strength may be changed. Positioning of the NMR probe may also be assisted by an ultrasound scan or by using known anatomy.

In some examples, the NMR probe may be configured to measure iron content. In such examples, the NMR signals may be measured at a single or various magnetic fields. Controlled-field electromagnet or repositionable permanent magnets may be used for the iron content measurement.

FIG. 4 illustrates a cross-section view of an example unilateral NMR apparatus and corresponding magnetic field distribution. Referring to FIG. 4, a configuration using two tapered permanent magnet blocks with opposite magnet orientations is shown. The example NMR probe may include magnet block 401 and RF antenna 403 configured with magnetic block orientation 402 and RF field orientation 404 to generate a sensitive volume 405. The magnetic field distribution 406 permeates the sensitive volume 405. For example, a "dipole" magnet array may be two blocks in opposite magnetization orientation on a ferromagnetic plate or yoke. The field distribution may be manipulated by the shape, magnetization, and/or orientation of the magnet blocks. Further changes in the field distribution may be achieved by using a set of gradient coils, a series of adjusting (or shimming) ferromagnetic "bottoms" or by placing an additional piece of magnet in the gap of the magnet pair. The permanent magnets may be optimized in shape and magnetization level of the permanent magnet blocks, to achieve a strong static magnetic field above the magnet array with a relatively low field gradient in the region of interest.

The field of such opposite-block configuration may be primarily parallel to the outer surface of the probe. The probe configuration may be optimized to produce flat surfaces of constant magnetic field amplitude. This has an advantage in terms of definition of a disc-shaped sensitive volume and helps on the accurate computation of diffusion parameters. The quantification of diffusion parameters may assist providing information on the mobility of the protons, thus helping discriminate between protons in various substances such as fat, water, and tissues.

In some examples, the RF antenna 405 may be a loop or spiral coil placed above or in the gap of the magnet array. The RF antenna may also be placed adjacent to or near the magnet. In that case, the magnet blocks may be made with a non-conducting bonding material in order to avoid interference with the RF antenna due to conductivity of the magnetic blocks. A RF antenna array may provide an effective way to transmit and receive signals to and from the sensitive volume.

The unilateral antenna may have a low Q factor to account for the conductivity of the subject's organic tissue. The RF antenna may be retuned manually or automatically after the probe is placed on or close to the body, correcting for tuning shifts generated by the presence of the electrical conductivity of the body. In some examples, an E-field shield may be used between the antenna and the body to minimize electric loading of the antenna 407.

Figure 4A:
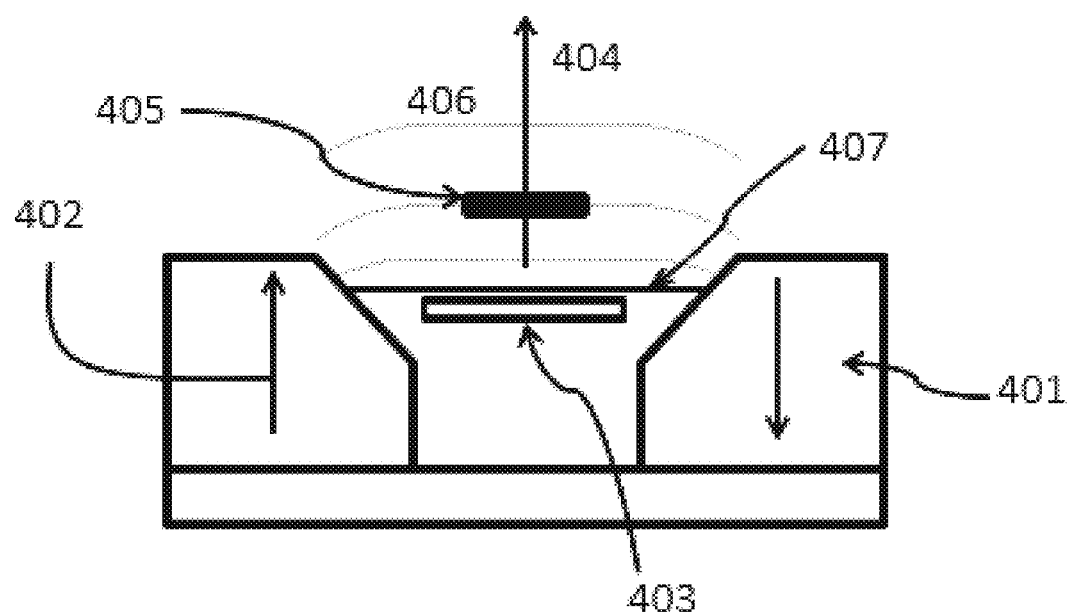
FIG. 4A is a schematic diagram illustrating a cross-section view of an example NMR apparatus and corresponding magnetic field distribution with a sensitive volume outside of the NMR probe, consistent with embodiments disclosed herein.
Figure 4B:
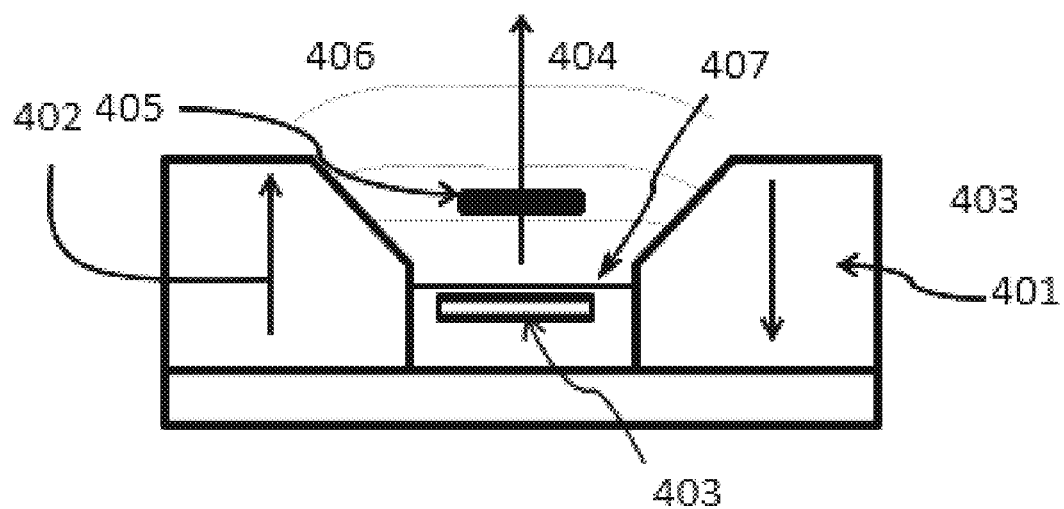
FIG. 4B is a schematic diagram illustrating a cross-section view of an example NMR apparatus and corresponding magnetic field distribution with a sensitive volume within the NMR probe, consistent with embodiments disclosed herein.

FIG. 4A shows a configuration where the sensitive volume 405 is outside the boundaries of the unilateral probe. While FIG. 4B shows a configuration where the sensitive volume 405 is inside the boundaries of the unilateral probe.

Figure 5:
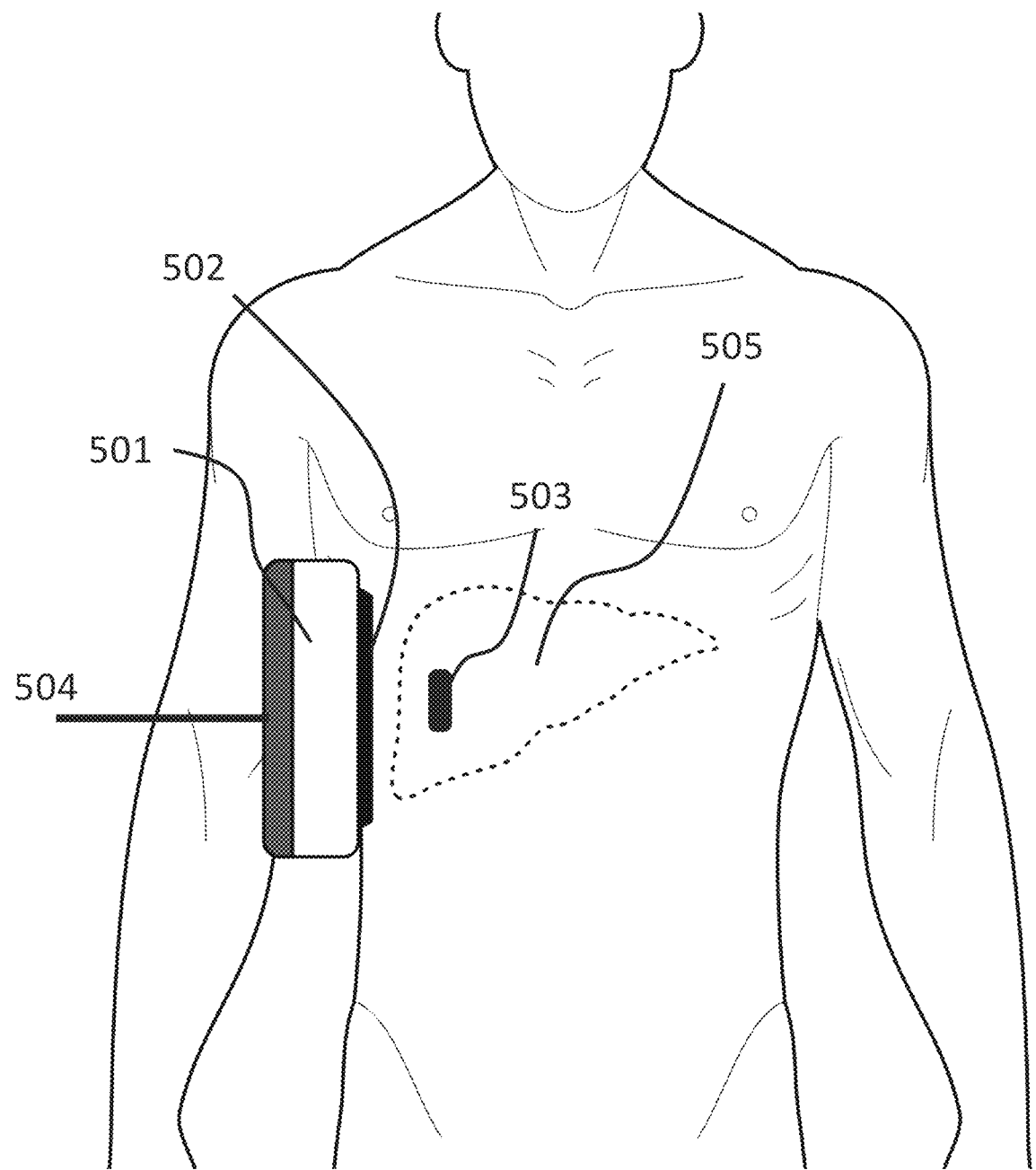
FIG. 5 illustrates an example NMR apparatus as applied to a human subject for purposes of measuring characteristics in the liver, consistent with embodiments disclosed herein. In this example, the sensitive volume is outside of the unilateral NMR probe.

FIG. 5 is an example representation of the positioning of the unilateral NMR probe in the proximity of a human liver. As shown, the sensitive volume of the unilateral NMR probe is outside of the probe and in the liver. As illustrated in FIG. 5, a unilateral magnet array 501 together with RF Antenna 502 may generate sensitive volume 503 in liver 505.

In some embodiments, a method of taking non-invasive and in-vivo measurements of a subject's organs using a unilateral NMR probe may include placing the NMR probe on or near by the body, in the proximity of the organ of interest. A scan may be performed while keeping the compact probe in place, without the need to apply pressure on the skin. The scan may be performed at a single, selected depth or a depth profile is manually or automatically attained (e.g., as shown in FIG. 3), by changing the frequency (proportional to the static magnetic field) or repositioning the probe.

Depth resolution may be attained by frequency encoding the acquired signal using a single, broadband excitation pulse or by using a series of pulses with different frequencies. The NMR probe may generate static and RF magnetic fields in a manner that NMR measurements are performed at selected depths into the body. The measurement may be performed at a single position and with a single frequency, determining properties of an organ at a specific volume inside of it. Measurements may also be performed at various frequencies in a single position (for example by changing the field strength generated by a magnet) to determine the iron content.

The time series of the NMR signal when using a sequence of RF pulses may be used to determine NMR relaxation times, diffusion parameters, and spectral discrimination. For example, the fat content may be determined by quantifying the relative amount of protons in fat to proton in water and other tissues (measurable by NMR). The quantification may be achieved by discriminating the NMR signals based on any or a combination of: relaxation times T1 (longitudinal or spin-lattice relaxation), T2 (transverse or spin-spin relaxation), diffusion parameters and J-coupling. The use of diffusion parameters may improve discrimination between the various tissues and water present in the sensitive volume.

In unilateral NMR, the NMR parameters may be measured in the presence of magnetic field gradients. Various pulse sequences may be used to measure biological, chemical, and physical properties of the tissue. For example, proton density, relaxation times, and diffusion parameters may be quantified with spin echo pulse sequences, which are effective even in the presence of inhomogeneous magnetic fields. Additionally, discrimination may be achieved using a dedicated J-coupling fat quantification pulse sequence. In fat suppression methods, the pulse spacing and pulse duration may be used to selectively reduce signal based on the proton spectral shift.

In some examples, the ratio of the number of protons of mobile triglycerides and the number of protons of mobile water and mobile triglycerides, or Proton Density Fat Fraction (PDFF), may be used to assist with the determination of liver fat content. PDFF may be determined based on a discrete multi-exponential analysis of the amplitude of the NMR signals. Differentiation of liver fat from other molecules may be based on different relaxation times of proton NMR signals from fat, water, and tissues. PDFF may be used as a biomarker of tissue fat concentration. Other ways of representing relative fat content may be used, such as the relative amplitude of signals from fat to water protons. These methods enable quantification of fat and iron content, without utilizing spectral information.

NMR signal amplitude is a measure of the proton density in the sensitive volume. For organs such as the liver, protons are present in water, fat, and surrounding tissues. In MRI and NMR, tissue discrimination may be achieved by determining the signal amplitude and characteristics lifetime (or relaxation time) of a multi-component signal, e.g., the aggregate of two or three exponential decaying signals, each of which has its own relative contribution to the total, measurable, signal. Mathematical methods allow for the deconvolution or separation of the individual contributions. This approach enables the quantification of protons from fat, water, and other tissues.

Spin-echo relaxation times in the presence of magnetic field gradients are biased by molecular diffusion, which may be used as a discrimination factor. Diffusion is readily measurable in the presence of inhomogeneous magnetic fields.

Unilateral magnets may have an associated field gradient that is significantly larger than that of clinical MRI instruments. Therefore, the present disclosure provides data acquisition performed in the presence of inhomogeneous fields. Accordingly, the lifetime of the observed signal or T2* is short (signals decay fast). Using spin echo techniques accommodate for the shorter observed signal. Using spin echo techniques, the NMR signals are refocused and may be observed after a longer period of time. A single spin echo may be attained with two RF pulses of calibrated durations. A sequence of multiple echoes is attained by utilizing a series of RF pulses.

The T2 relaxation time from an NMR echo train or Hahn-echo and T1 relaxation time may be measured with the NMR probe disclosed herein. Embodiments disclosed herein use the diffusion parameter to provide information on the mobility of the protons or other nuclei in water, fat and various tissues. In the presence of field gradients, the effective decay time during a multi pulse sequence, e.g., Carr-Purcell-Meiboom-Gill (CPMG)—may be represented as:

$$1/T2\text{eff} = 1/T2 + A\,TE^2,$$

where T2eff is the measured relaxation time (lifetime of the signal decay in a time series of the spin echo or Hahn echo in a two pulse measurement), T2 is the spin-spin relaxation time, TE is the inter-spin echo duration (echo time), and A is a parameter determined by the magnetic field gradient (G) and the diffusion parameter (D) of the observed tissue. If the gradient is constant over the sensitive volume, A is proportional to $D\,G^2$. Therefore, the signal decay along a train of RF pulses provides information on T2 as well as diffusion. In one embodiment, diffusion effects may be reduced by running multi-echo pulse sequences with short time windows between RF pulses. The analysis including diffusion may be used to accurately compute T2 in the presence of large field gradients. If this is not taken into consideration, the measured relaxation time in the multi-echo sequence is shorter than T2.

Performing NMR measurements at two or more TE durations allows for the independent computation of the diffusion constant and T2, as the magnetic field gradients are known. This provides an advantage as it allows to measure decay times analytically removing the effect of diffusion. As an added value, the diffusion parameter may be used as another factor to discriminate between, e.g., water, fat, and other tissues.

For a multi-component signal (e.g. protons from fat, water and others), the total signal amplitude in a time series in a CPMG sequence (or similar multi-pulse sequence) may be represented as a continuous distribution of decaying signals or a discrete distribution of individual signals as follows:

$$S(t) = C_1 e^{-t/T2\text{eff}_1} + C_2 e^{-t/T2\text{eff}_2} + C_3 e^{-t/T2\text{eff}_3} + \ldots + C_0,$$

where t is the time along the pulse sequence, C represents the relative contribution of each component and $C_0$ represents the baseline signal. In a two component case:

$$S(t) = C_1 e^{-t/T2\text{eff}_1} + C_2 e^{-t/T2\text{eff}_2} + C_0,$$

with $1/T2\text{eff}_1 = 1/T2_1 + A_1 TE^2$ and $1/T2\text{eff}_2 = 1/T2_2 + A_2 TE^2$.

The diffusion parameters are proportional to the corresponding $A_1$ and $A_2$ parameters for each of the components. In the two-component example, a double exponential fit to the data may generate the data used to compute the relative concentration of each component, the T2 relaxation time and the diffusion parameters. The relative concentration of a component, such as fat, may be expressed as a ratio, C1/C2, or as the following ratios:

$$C_1/(C_1+C_2) \text{ and } C_2/(C_1+C_2) \text{ or } C_1/(C_1+C_2+C_0) \text{ and } C_2/(C_1+C_2+C_0).$$

The computation of C1 and C2 may be determined by resolving the independent equations shown above or by resolving the various equations simultaneously.

In other examples, a 2-dimensional (2D) map of the T2 and diffusion parameter may be plotted after using dedicated pulse sequences and analysis. The combination of T2 and diffusion information enables the visualization of various contributions to the signal, e.g. water, fat, and other tissues.

In some embodiments, absolute fat concentration may be determined using the unilateral NMR probe. For example, the NMR probe may be calibrated using historical proton concentration data or using a normalization factor post processing. This method is based on the property that the shape and volume of the sensitive volume is essentially unchanged when frequency and RF pulses are unchanged between the calibration and the measurement of the target organ. Corrections may be performed if electrical loading of the body are observed and measured during the diagnostic procedure.

By measuring the relative amplitude of protons in fat signals and protons in water, the fat-to-water ratio may be calculated. NMR measurements at specific depths in the body and depth profiles of NMR parameters may be used to quantify the fat content. NMR signals may also be observed as generated by protons in surrounding tissues. Depending on the NMR setup, signal may be observed from bond protons, which typically have a faster decay time. These signals are obscured in instruments that do not focus on fast decaying signals. The unilateral NMR instrument may be furnished with a RF antenna and receiver that are capable of detecting fast decaying signals, allowing for the observation of proton and other elements bonded or chemically linked to various tissues and even solid components.

The measurement of specific organ properties—e.g. fat content—may be performed by using dedicated pulse sequences that enhances or decimates signals with specific relaxation times. As an example, T1 contrast (signal bias) may be achieved by changing the repetition rate in the pulse sequence or using a single or multiple saturation pulses before the pulse sequence is launched.

Figure 6:
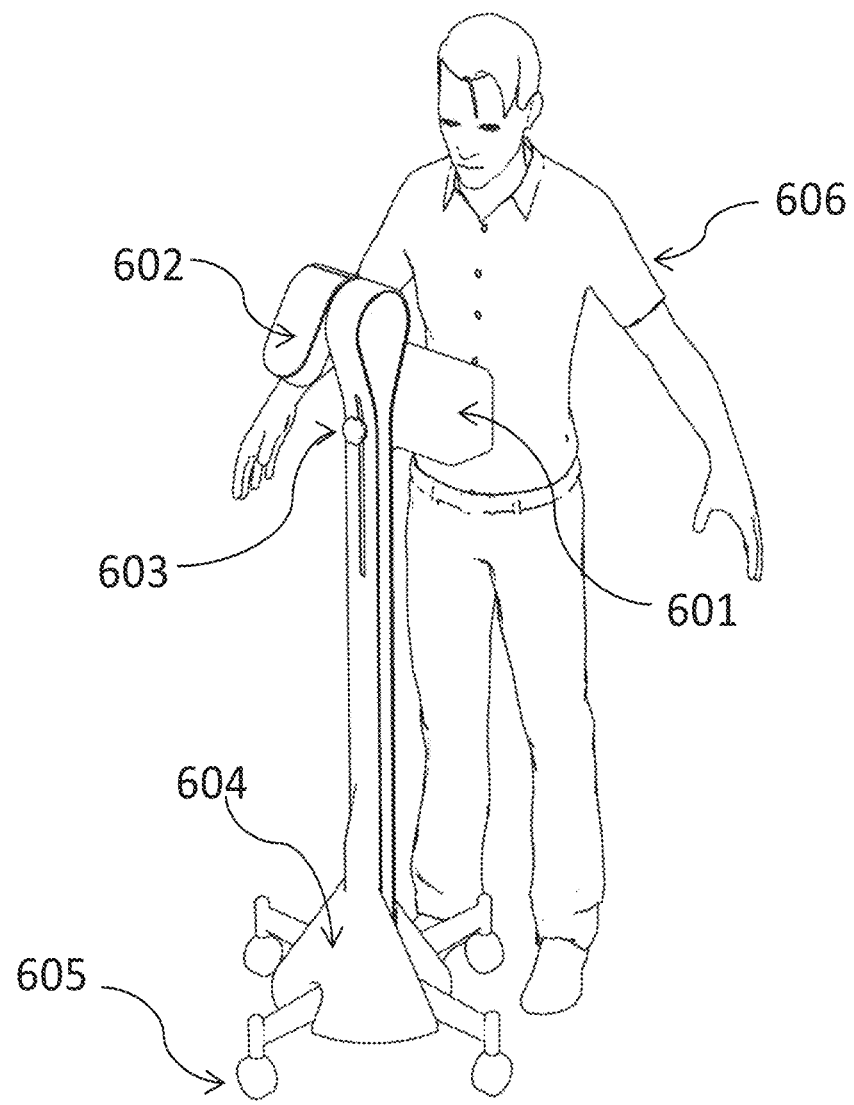
FIG. 6 illustrates an example NMR apparatus as applied to a human subject, consistent with embodiments disclosed herein.
Figure 7A:
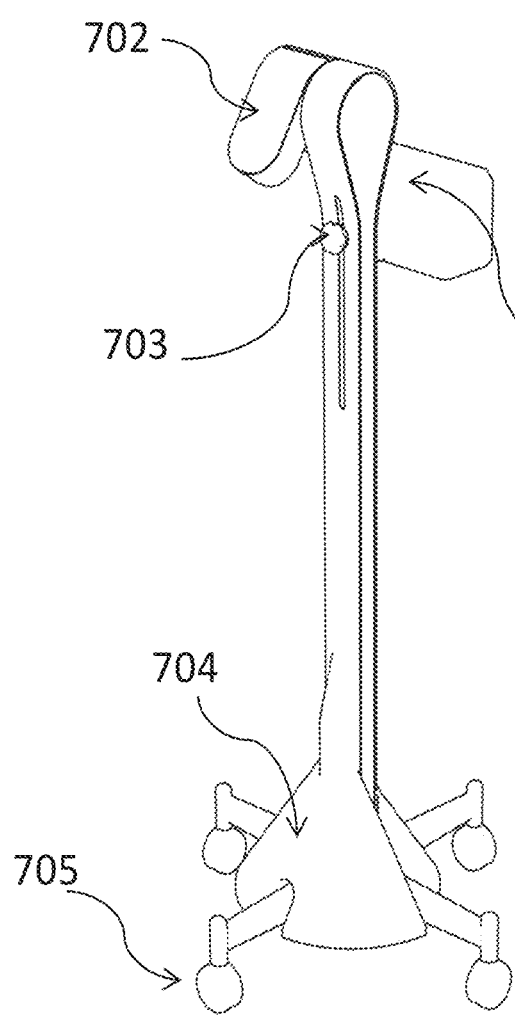
FIG. 7A illustrates a perspective right-side view of an example NMR apparatus, consistent with embodiments disclosed herein.
Figure 7B:
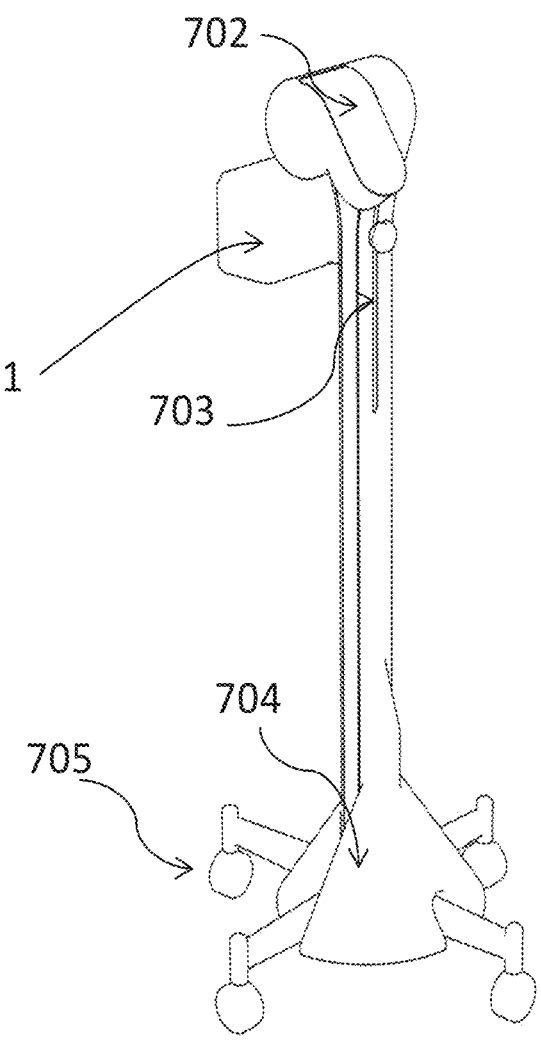
FIG. 7B illustrates a perspective left-side view of an example NMR apparatus, consistent with embodiments disclosed herein.
Figure 8A:
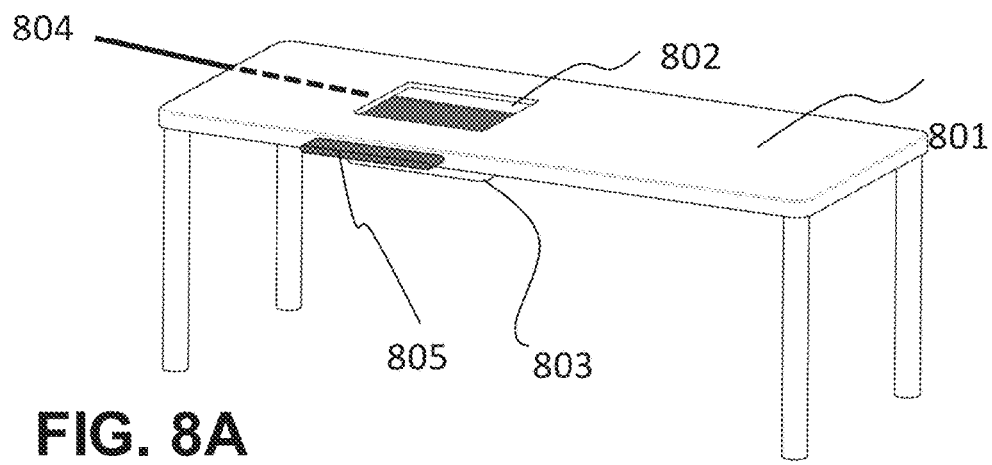
FIG. 8A illustrates a perspective view of an example table-based NMR apparatus for purposes of measuring characteristics of a subject's organ, consistent with embodiments disclosed herein. In this example the probe is positioned underneath the table.
Figure 8B:
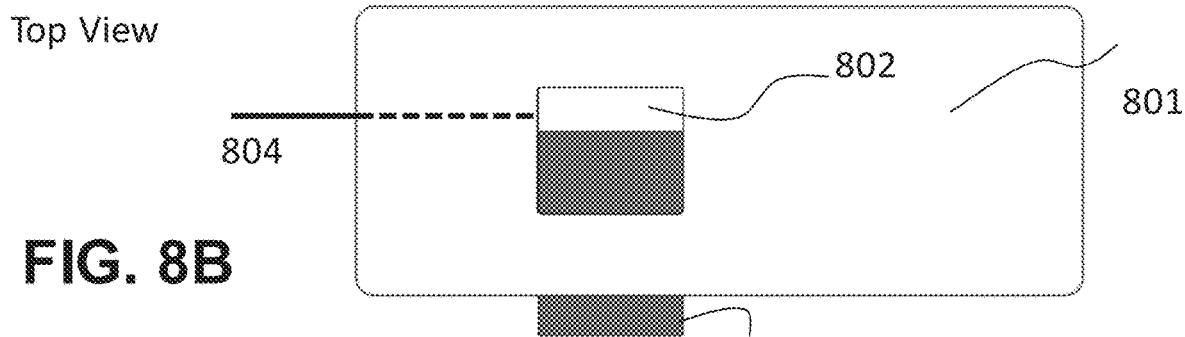
FIG. 8B illustrates a top view of an example table-based NMR apparatus for purposes of measuring characteristics of a subject's organ, consistent with embodiments disclosed herein. In this example the probe is positioned underneath the table.
Figure 8C:
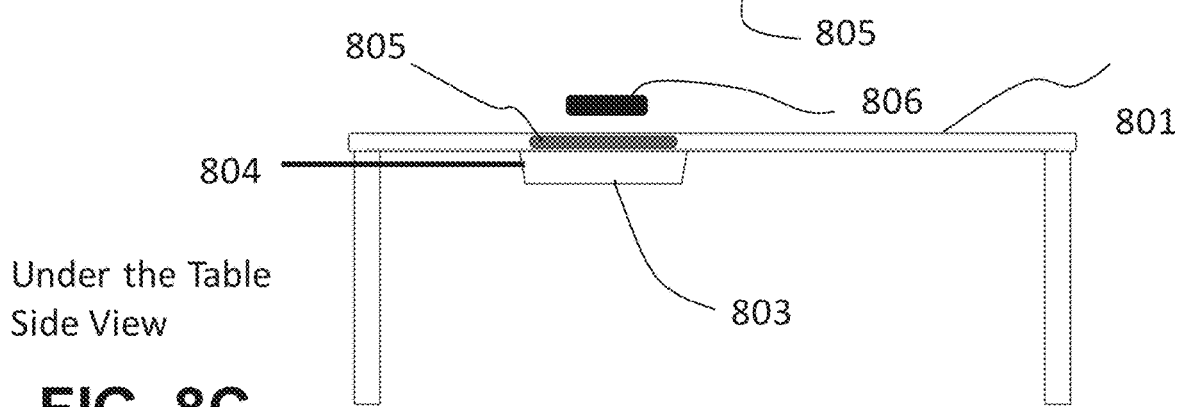
FIG. 8C illustrates a side view of an example table-based NMR apparatus, with the NMR probe positioned underneath the table, for purposes of measuring characteristics of a subject's organ, consistent with embodiments disclosed herein.
Figure 8D:
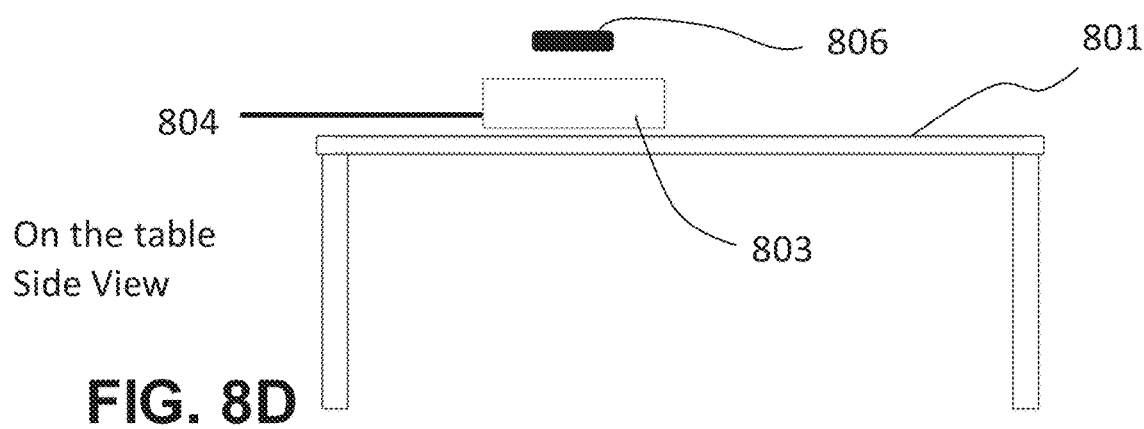
FIG. 8D illustrates a side view of an example table-based NMR apparatus, with the NMR probe positioned on top of the table, for purposes of measuring characteristics of a subject's organ, consistent with embodiments disclosed herein.

FIGS. 6 through 9 illustrate embodiments of the disclosed technology. For example, FIGS. 6 and 7 show a compact configuration where the patient may stand while measurements are taken with the NMR probe. As illustrated, NMR probe head 601 may be positioned against or in proximity to a subject. User interface 602 may accept input from a user for purposes of setting system parameters and configuring the NMR probe, and may display NMR signals and results. A height adjustment mechanism 603 may enable adjustments of the NMR probe position relative to the subject and target organ. The wheeled probe 601 may be positioned on or in proximity to the body, in the proximity of the liver or other organs. The probe 601 height may be adjusted according to the height of the patient. The wheels 605 may be locked to avoid displacement of the instrument while the measurements are performed.

Similarly, various views of the apparatus shown in FIG. 6 are presented in FIG. 7. The NMR probe 701 may be tattered to a compact control unit. The apparatus has a control console/user interface, with buttons or a touch screen that triggers a measurement.

In some embodiments of the disclosure, a permanent magnet array generating magnetic fields parallel to the top of the probe head, with a contained stray field and a moderate depth gradient, may be used to attain depth profiles. The magnet array may be built with NdFeB magnetic material. SmCo and other magnetic alloys with adequate temperature characteristics may also be used.

Example NMR probe designs may be configured for safety by keeping the magnetic field confined to a small region around the probe head. When not used, the NMR probe head may be completely or partially covered with a ferromagnetic or high permeability material to effectively contain the magnetic field, addressing issues of safety.

Figure 9A:
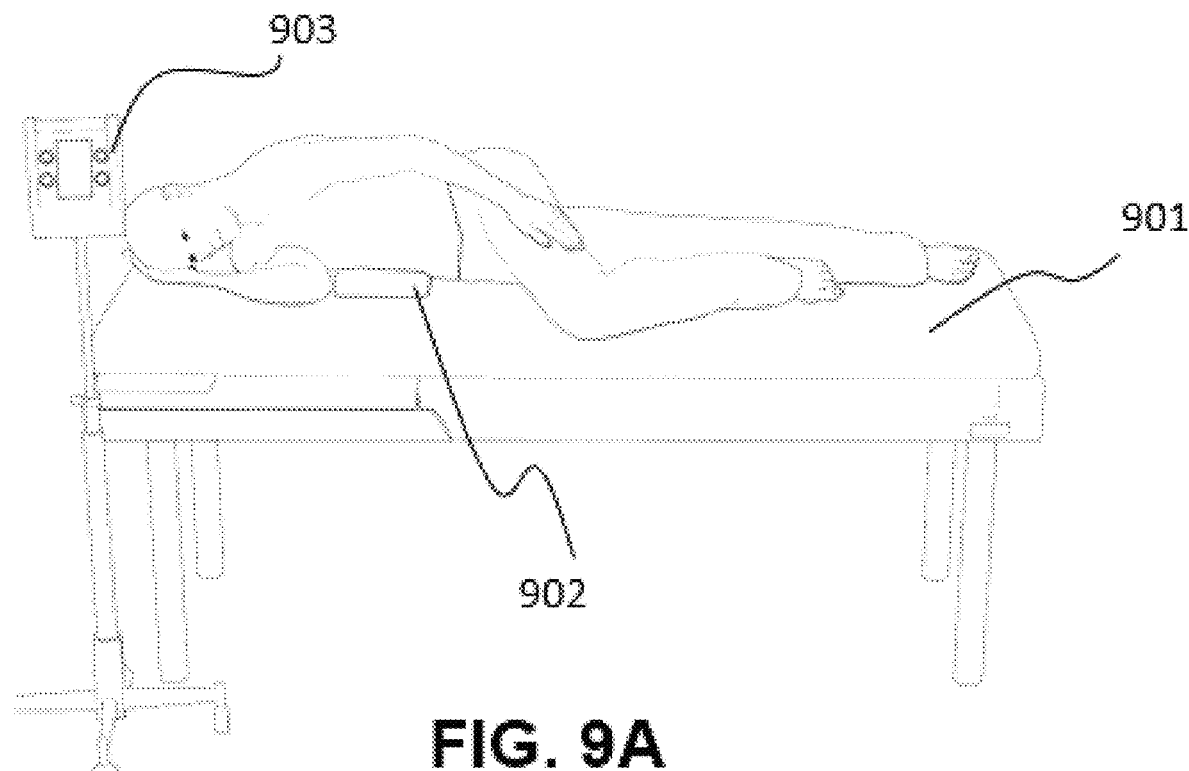
FIG. 9A illustrates a perspective view of an example table-based NMR apparatus with the NMR probe positioned on the table for purposes of measuring characteristics of an internal organ of a human subject, consistent with embodiments disclosed herein.
Figure 9B:
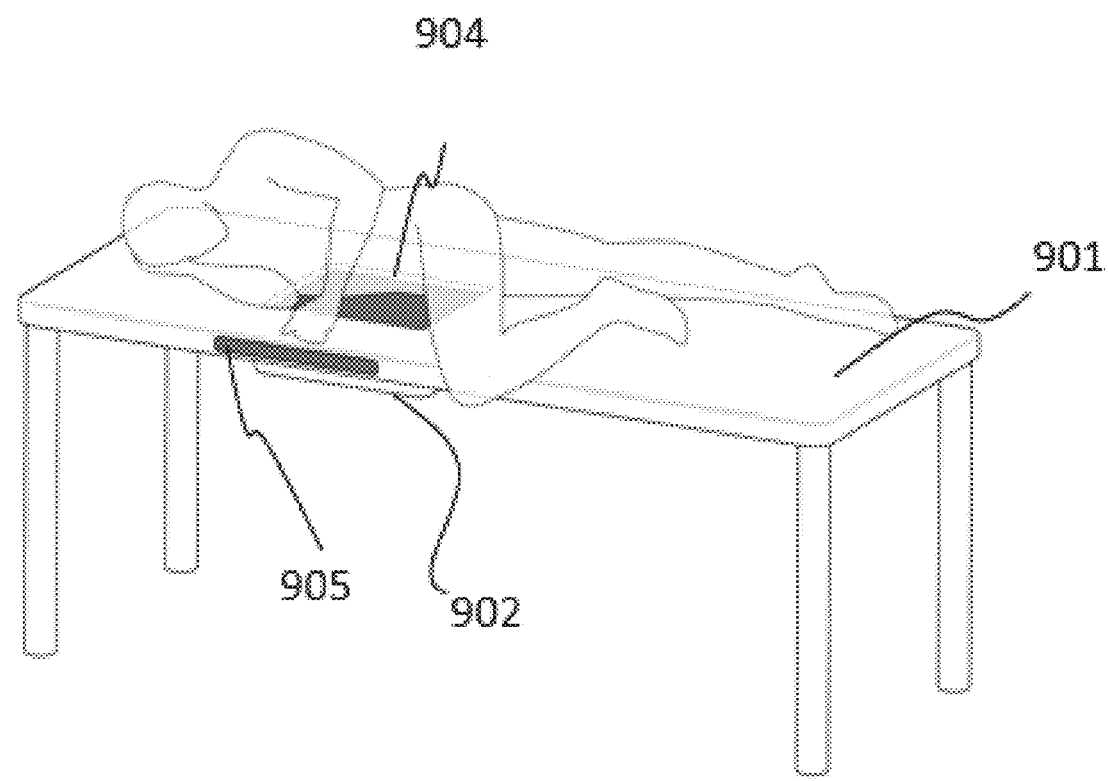
FIG. 9B illustrates a perspective view of an example table-based NMR apparatus with the NMR probe positioned underneath the table for purposes of measuring characteristics of an internal organ of a human subject, consistent with embodiments disclosed herein.

Referring to FIG. 8 and FIG. 9, a compact probe may be mounted under a bed or placed on the bed. The NMR probe may generate a sensitive volume above the probe or within the boundaries of the probe, in accordance with an alternate embodiment of the present disclosure. As can be seen, a patient Table 801, a Probe Opening 802, a Probe 803, Control and Data Line 804, a Retractable Probe Cover 805, and Sensitive Volume 806 are shown. The probe 803 may be mounted under the bed or placed on the bed and the sensitive volume 806 is located above the probe. The patient 902 may be positioned in a way that the area on the side of the chest—near the liver—is above the Probe 903, as shown in FIG. 9. The patient Table 901 may have integrated Retractable Probe Cover 905 that effectively blocks the magnetic field when is shut—when the apparatus is not in use. This is a safety feature that is easily incorporated using a high permeability or ferromagnetic material that contains the magnetic field when desired. For the probe placed on the table or bed, the magnet may be covered with a ferrous or other high permeability cover—allowing for the probe to be safely moved or kept on the bed.

Figure 10:
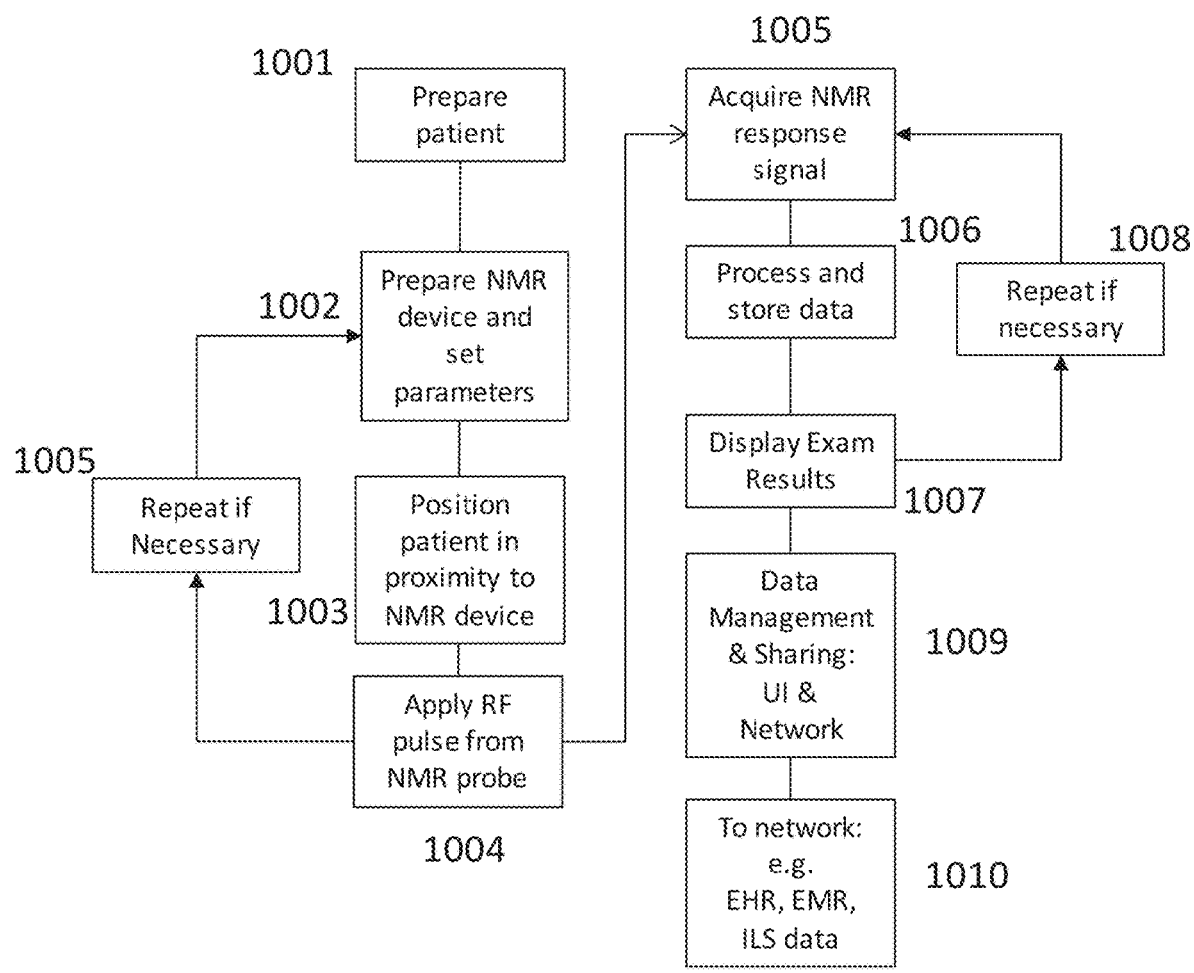
FIG. 10 is a flow chart illustrating an example process for non-invasive and in-vivo measurement, screening, and/or diagnosis of characteristics of a subject's organ using an open NMR apparatus, consistent with embodiments disclosed herein.

FIG. 10 illustrates an example diagnostic protocol for non-invasive and in-vivo NMR measurement using a unilateral NMR probe. For example, a liver exam may be based on fat, iron, or another exam may be based on sodium content in tissue. As illustrated, the procedure may include the preparation of the patient at step 1001. This may include, for example, removal of the shirt and using pants free of metallic components. The NMR probe may then prepared for the specific exam to be performed at step 1002. This may include setting parameters to target a proper depth into the body and selection of specific data collection protocols, for example, using a GUI communicatively coupled to the NMR probe. The method may also include positioning the NMR probe on or near the body of the patient, by the organ being examined at step 1003. The method may also include taking a preliminary examination at step 1004 to assist in determining proper positioning. If the results of the preliminary exam show issues (such as erroneous positioning), the operator may reset the positioning of the patient and/or device parameters at step 1002.

The method may include performing the diagnostic procedure by initiating the data acquisition at step 1005. The data acquisition may range from a single channel RF signal collection to dual channel RF acquisition to collecting signal from multiple antennas in a RF antenna array. If an RF antenna array is utilized, the amplitude and phase of the signals from each element is measured and processed.

In some examples, the start of the exam may be as simple as pressing a START option on a GUI. The method may include processing acquired data at step 1006 and storing the results. As an option, the raw data may also be stored for post-processing as necessary. The GUI may display the results of the exam at step 1007. The result may, for example, be a simple value indicating the fat content in an organ such as the live. If problems arise from the results or if additional data is necessary, the operator may be re-initiate the data acquisition process at step 1008.

In some embodiments, stored data may be integrated into a medical record or shared with medical professionals. For example, the data may be transferred to a portable device such as a flash memory stick or it may be accessed from a remote location. Remote access may be performed wirelessly or by a wired network, for example via USB or Ethernet. The data may be electronically shared at step 1010 as part of the electronic health record (EHR) and/or electronic medical record (EMR) of the patient. The diagnostic results may be part of the medical and treatment history of the patient. The format may be for example in accordance with Integrated Laboratory Systems (ILS).

In some examples, a data bank may keep information of the clinical diagnostic data. The data may contain other information as age of the patient, Body Mass Index, weight, region and others. The data bank may be used for example to "learn" trends and managing medical risk. The process to manage and analyze the data could include machine learning and artificial intelligence processing. As the "big data" bank may be continuously fed with results from more exams, the algorithms would refine the output over time, as they "learn" the efficacy of the prediction. The data bank also allows to directly compare a result with that of other patients or groups of patients.

The availability of trend information from a data sharing approach allows for custom treatments. Also, if the data includes patients under treatment with drugs, the information may be utilized to gauge the efficacy of drugs in the market or entering the market. Correlation may be found between the efficacy and specific population groups.

Figure 11A:
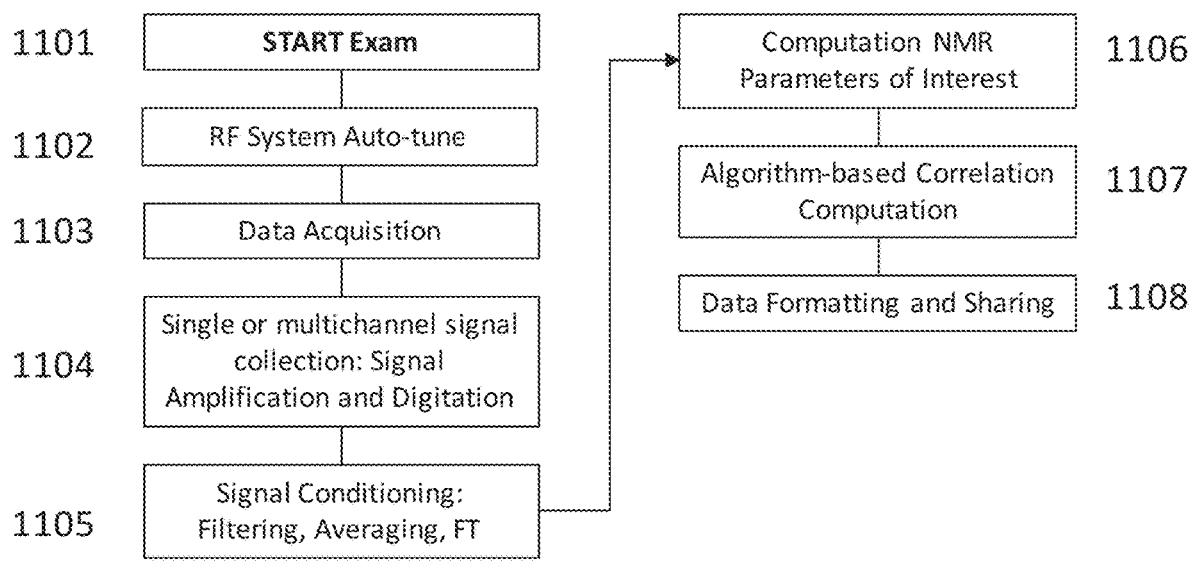
FIG. 11A is a flow chart illustrating an example process for non-invasive and in-vivo measurement, screening, and/or diagnosis of characteristics of a subject's organ using an open NMR apparatus, consistent with embodiments disclosed herein.

FIG. 11 illustrates an example non-invasive in-vivo NMR examination. As illustrated in FIG. 11A, the process may be automatically initiated or manually-triggered at step 1101. Once the patient is in place, the RF system may be auto-tuned. The antenna electromagnetic characteristics may be affected by the presence of the electrically conductive human body. The instrument may quantify the effect and optimize the antenna characteristics before starting with the power transmission and signal collection at step 1103. In some examples, the received RF signals may be modulated and amplified with low noise electronics. Once the signal is collected and digitized—analog or digital signal processing may also be performed. The signal may be conditioned at step 1105. RF filters may be applied to the signals to discard unwanted signals that reduce the accuracy and precision of the results. The performance may be improved by signal averaging, which increases the signal-to-noise-ratio of the signal. Fourier Transformation of the data (FT or Fast Fourier Transform FFT) may also help in selecting signal at the frequency of interest and adding contributions of the signal over a selected time window.

In some embodiments, a series of parameters of interest may be computed at step 1106. For example, parameters of interest may include the signal amplitude, the relaxation times (T2, T1, T2*), J-coupling and diffusion coefficient. Typical T1 relaxation times may range from tens of milliseconds to the order of 1 second. T2 is generally shorter than T1. One or more parameters of interest may be correlated to clinically relevant information at step 1107. For example, a multi-exponential decay of the NMR signal may be used to compute the relative amount of fat in organisms like the liver. Processed data may be formatted and shared at step 1108. In some examples, the output of the NMR probe may be the raw or processed NMR data, which may be analyzed at a later stage by a medical professional. In some embodiments, results may be displayed on a GUI when the exam is completed. As an example, the relative or absolute fat content in the liver may be displayed.

Figure 11B:
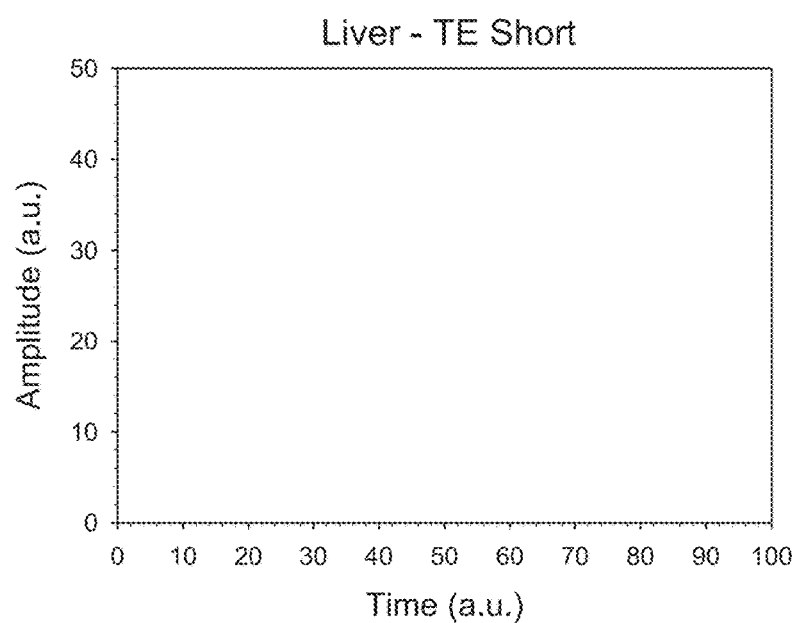
FIG. 11B is a chart illustrating an example time series of the amplitude of the NMR signal in a multi-pulse sequence and a two exponential decay fitting to data collected in accordance with the process illustrated in FIG. 11A as applied to an animal liver with a high content of fat.

As an example, FIG. 11B shows the time series of a multi-echo CPMG pulse sequence. This sequence allows manipulation RF pulse and signal phases to effectively reduce unwanted spurious background signals and therefore increase signal to noise ratio.

In some instances, sensitivity may be increased, which in turn improves precision and accuracy, using signal averaging. For example, instead of collecting a single time series of the signal amplitude, the acquisition may be repeated several times. The data is then added or averaged. If the noise is incoherent (for example white Gaussian noise), the signal to noise ratio increases approximately as the square root of the number of scans. As one consideration to this signal averaging process, the spins from the nucleus of the atoms should significantly or fully "recover" or repolarize after each acquisition. The time scale for the repolarization is the relaxation time called T1.

In some examples, signal-to-noise ratio may be improved by collecting unwanted interfering far-field RF signals using a separate set of antennae. The RF interference may be suppressed by mathematically subtracting the signals correlated to the far fields, while keeping the signals of interest.

In some examples, signal-to-noise ratio may be improved by applying filters, such as match filtering or Hanning windows. The time series or the Fourier Transform data may be modulated by the expected response.

Figure 12A:
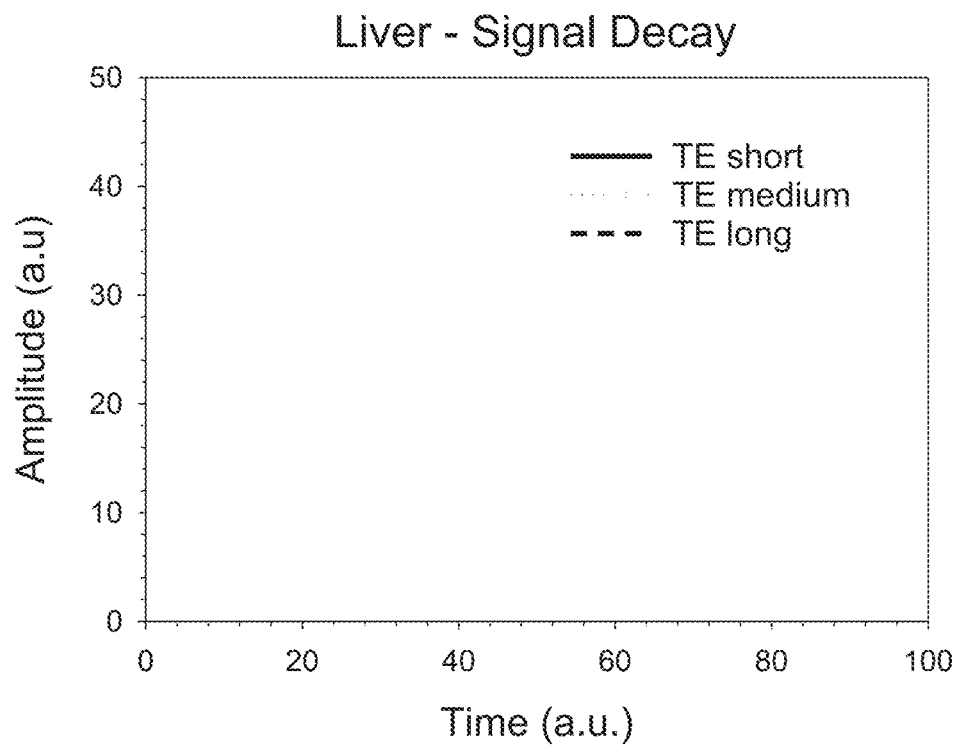
FIG. 12A is a chart illustrating three time series of NMR signals in a multi-pulse sequence, collected in accordance with embodiments disclosed herein, where the time between the RF pulses is changed.
Figure 12B:
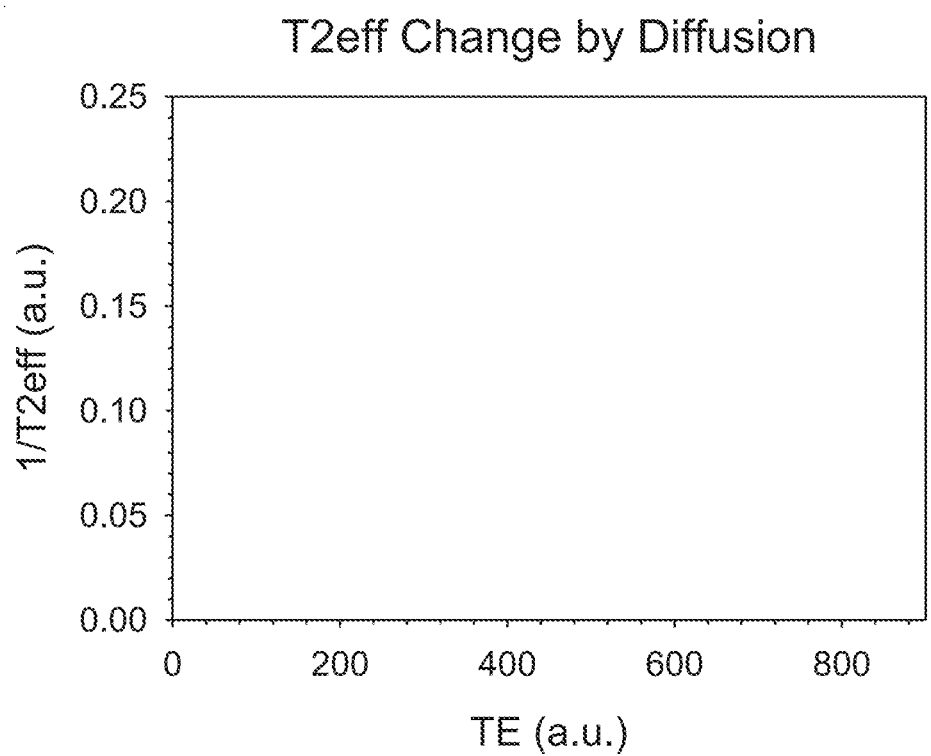
FIG. 12B is a chart illustrating a change of NMR signal decay time with the pulse spacing in a multi-pulse sequence as used to compute a diffusion parameter in accordance with embodiments disclosed herein.

The plot in FIG. 11B shows the amplitude of each of the echoes and a double exponential fit to the time-series data, with a statistical Coefficient of Determination of $R^2=0.97$. The dual decay observed is driven by different relaxation times for fat and for water and other tissues. The two exponential decaying signals add to the observed signal decay. The results for the regression for three different spacing between RF pulses are shown in FIG. 12. This plot shows how the effect of diffusion produces a faster decay, which is quantifiable by the analysis presented in this disclosure. The example illustrated in FIG. 11 and FIG. 12 results in a ratio of fat to water and other observable tissues of $C_1/(C_1+C_2)=0.40$. The diffusion parameters are computed by a fitting to the data for each of the components—FIG. 12B shows the fitting using three pulse separations (or echo times). The ratio of diffusion parameter is calculated as $D_1/D_2=A_1/A_2$. In this case $D_1/D_2=1.7$. This indicates that the fast decaying component has a diffusion parameter 70% higher than that of the slow decaying component. The analysis extends to more than two components.

The ratio may be corrected for diffusion effects in the presence of inhomogeneous static magnetic fields, as explained in this disclosure. The pulse sequence with the shortest interval between RF pulses provides the fat ratio that is closest to the corrected value, as longer pulse separations show more pronounced diffusion effects.

Figure 13:
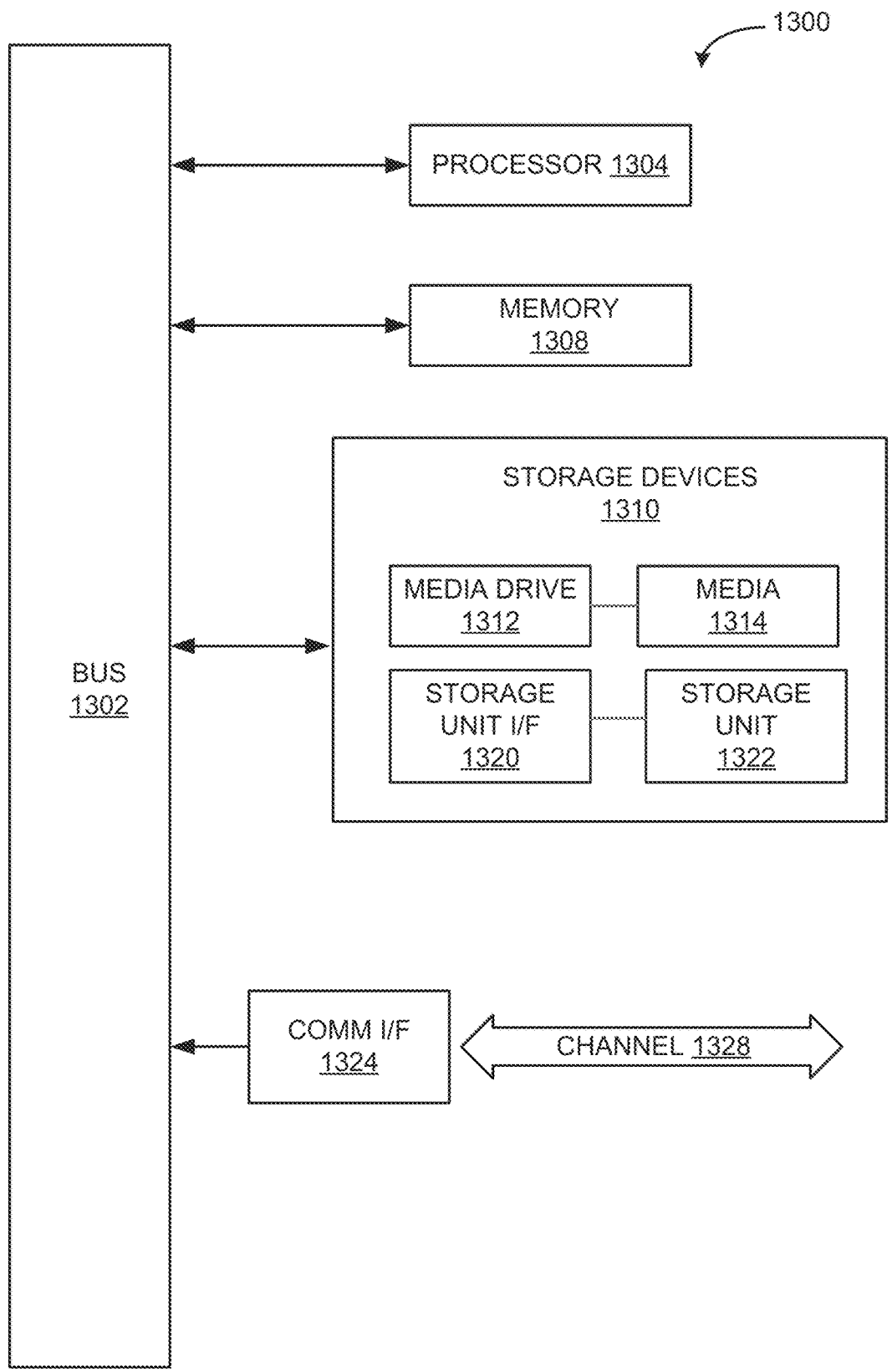
FIG. 13 is a diagram illustrating an exemplary computing module that may be used to implement any of the embodiments disclosed herein.

As used herein, the term logical circuit or component might describe a given unit of functionality that can be performed in accordance with one or more embodiments of the technology disclosed herein. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component or logical circuit. In implementation, the various components or logical circuits described herein might be implemented as discrete components or the functions and features described can be shared in part or in total among one or more components or logical circuits. In other words, as would be apparent to one of ordinary skill in the art after reading this description, the various features and functionality described herein may be implemented in any given application and can be implemented in one or more separate or shared components in various combinations and permutations. As used herein, the term logical circuit may describe a collection of components configured to perform one or more specific tasks. Even though various features or elements of functionality may be individually described or claimed as separate components or logical circuits, one of ordinary skill in the art will understand that these features and functionality can be shared among one or more common software and hardware elements, and such description shall not require or imply that separate hardware or software components are used to implement such features or functionality.

Where logical circuits, components, or components of the technology are implemented in whole or in part using software, in one embodiment, these software elements can be implemented to operate with a computing or processing component capable of carrying out the functionality described with respect thereto. One such example computing component is shown in FIG. 13. Various embodiments are described in terms of this example—computing component 1300. After reading this description, it will become apparent to a person skilled in the relevant art how to implement the technology using other computing components or architectures.

Referring now to FIG. 13, computing component 700 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing component 1300 might also represent computing capabilities embedded within or otherwise available to a given device. For example, a computing component might be found in other electronic devices such as, for example, digital cameras, navigation systems, cellular telephones, portable computing devices, modems, routers, WAPs, terminals and other electronic devices that might include some form of processing capability.

Computing component 1300 might include, for example, one or more processors, controllers, control components, or other processing devices, such as a processor 1304. Processor 1304 might be implemented using a general-purpose or special-purpose processing logical circuits such as, for example, a microprocessor, controller, or other control logic. In the illustrated example, processor 1304 is connected to a bus 1302, although any communication medium can be used to facilitate interaction with other components of computing component 1300 or to communicate externally.

Computing component 1300 might also include one or more memory components, simply referred to herein as main memory 1308. For example, preferably random access memory (RAM) or other dynamic memory might be used for storing information and instructions to be executed by processor 1304. Main memory 1308 might also be used for storing temporary variables or other intermediate information during execution of instructions to be executed by processor 1304. Computing component 1300 might likewise include a read only memory ("ROM") or other static storage device coupled to bus 1302 for storing static information and instructions for processor 1304.

The computing component 1300 might also include one or various forms of information storage devices 1310, which might include, for example, a media drive 1312 and a storage unit interface 1320. The media drive 1312 might include a drive or other mechanism to support fixed or removable storage media 1314. For example, a hard disk drive, a floppy disk drive, a magnetic tape drive, an optical disk drive, a CD or DVD drive (R or RW), or other removable or fixed media drive might be provided. Accordingly, storage media 1314 might include, for example, a hard disk, a floppy disk, magnetic tape, cartridge, optical disk, a CD or DVD, or other fixed or removable medium that is read by, written to or accessed by media drive 1312. As these examples illustrate, the storage media 1314 can include a computer usable storage medium having stored therein computer software or data.

In alternative embodiments, information storage mechanism 710 might include other similar instrumentalities for allowing computer programs or other instructions or data to be loaded into computing component 1300. Such instrumentalities might include, for example, a fixed or removable storage unit 1322 and an interface 1320. Examples of such storage units 1322 and interfaces 1320 can include a program cartridge and cartridge interface, a removable memory (for example, a flash memory or other removable memory component) and memory slot, a PCMCIA slot and card, and other fixed or removable storage units 1322 and interfaces 1320 that allow software and data to be transferred from the storage unit 722 to computing component 1300.

Computing component 1300 might also include a communications interface 1324. Communications interface 1324 might be used to allow software and data to be transferred between computing component 1300 and external devices. Examples of communications interface 1324 might include a modem or softmodem, a network interface (such as an Ethernet, network interface card, WiMedia, IEEE 802.XX, or other interface), a communications port (such as for example, a USB port, IR port, RS232 port, Bluetooth® interface, or other port), or other communications interface. Software and data transferred via communications interface 1324 might typically be carried on signals, which can be electronic, electromagnetic (which includes optical) or other signals capable of being exchanged by a given communications interface 1324. These signals might be provided to communications interface 1324 via a channel 1328. This channel 1328 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 1308, storage unit 1320, media 1314, and channel 1328. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 1300 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

I claim:

1. A Nuclear Magnetic Resonance ("NMR") apparatus comprising:
   a unilateral magnet;
   a Radio Frequency ("RF") circuit;
   an RF antenna; and
   an NMR analytics logical circuit communicatively coupled to the RF circuit;
   wherein the unilateral magnet is shaped to generate a static magnetic field that extends into an internal organ of a subject when the unilateral magnet is configured to be positioned against or in proximity to a measurement area of the subject, the magnetic field shaped to generate a sensitive volume within a target region of the internal organ;
   the RF circuit and antenna are configured to:
   transmit one or more RF pulses into the target region;
   receive a first set of NMR signals generated by a first set of atomic nuclei from a first substance as the first set of nuclei realign their spin axes to the magnetic field after being stimulated by the RF pulses;
   receive a second set of NMR signals generated by a second set of atomic nuclei from a second substance as the second set of nuclei realign their spin axes to the magnetic field after being stimulated by the RF pulses; and
   the NMR analytics logical circuit is configured to:
   obtain the first and second sets of NMR signals, wherein an amplitude of the NMR signals is a measure of proton density; and
   quantify and characterize the first and second substances based on a discrete multi-component analysis of the first and second sets of NMR signals;
   wherein the discrete multi-component analysis comprises:
      determining first set of NMR relaxation times from the first set of NMR signals;
      determining a second set of NMR relaxation times from the second set of NMR signals;
      determining a first set of recovery times form the first set of NMR signals;
      determining a second set of recovery times from the second set of NMR signals;
      determining an independent first diffusion parameter from the first set of NMR signals;
      determining an independent second diffusion parameter from the second set of NMR signals;
      determining a J-coupling relationship between the first substance and the second substance based on a comparison of the first set of NMR signals and the second set of NMR signals wherein the comparison is based on detected nucleic interaction and resultant electron cloud distortion in the first and second sets of NMR signals caused by application of RF pulse sequences with pulse spacings determined by a time scale characteristic of the J-coupling analysis;
      determining whether the first substance is fat based on the discrete multi-component analysis;
      determining whether the second substance is fat based on the discrete multi-component analysis;
      determining whether the first substance is iron based on the discrete multi-component analysis; and
      determining whether the second substance is iron based on the discrete multi-component analysis.

2. The apparatus of claim 1, wherein the analytics logical circuit is further configured to perform a measurement of selected properties of the organ or other internal organs of the subject by using dedicated pulse sequences to enhance or decimate signals with specific relaxation times.

3. The apparatus of claim 1, wherein determining the J-coupling relationship further comprises using a dedicated fat quantification pulse sequence to discriminate a fat content of the internal organ.

4. The apparatus of claim 1, wherein the NMR analytics logical circuit is further configured to quantify a concentration of the first substance based on a discrete multi-component signal decay analysis of the first and second NMR signals.

5. The apparatus of claim 1, wherein the RF antenna comprises an open coil and is configured to transmit RF pulses in a substantially perpendicular orientation to the static magnetic field.

6. The apparatus of claim 1, wherein the RF antenna comprises an array of sub-antennas and is configured to transmit RF pulses in a substantially perpendicular orientation to the static magnetic field.

7. The apparatus of claim 1, wherein the analytics logical circuit is further configured to calculate and to plot, on a graphical user interface, a 2-dimensional map of T2 relaxation times and diffusion parameters from the first and second sets of NMR signals, showing the contributions of the first and second substances to the first and second sets of NMR signals.

8. The apparatus of claim 1, wherein the analytics logical circuit is further configured to calculate and to plot, on a graphical user interface, a 2-dimensional distribution of T1 recovery times and diffusion parameters from the first and second sets of NMR signals.

9. The apparatus of claim 1, wherein the analytics logical circuit is further configured to determine a fat concentration based on a ratio of the amplitude of the first set of NMR signals as compared with the amplitude of the second set of NMR signals.

10. The apparatus of claim 1, wherein the analytics logical circuit is further configured to obtain, from a NMR signal database, a calibration signal amplitude for fat in the organ and determine an absolute fat concentration based on a ratio of the amplitude of the first set of NMR signals as compared with the calibration signal.

11. The apparatus of claim 1, wherein the internal organ is a human liver.

12. The apparatus of claim 1, wherein the unilateral magnet comprises an electromagnet or a permanent magnet.

13. The apparatus of claim 1, wherein the unilateral magnet is a hand portable magnet or a standalone magnet.

14. The apparatus of claim 1, wherein the unilateral magnet is mechanically coupled to a pedestal or cart.

15. The apparatus of claim 1, wherein the unilateral magnet is mechanically coupled to a table or a retractable arm.

16. The apparatus of claim 1, wherein the NMR analytics logical circuit is further configured to determine a concentration of a target chemical element in the organ or one or more other internal organs in the subject, based on the first set of NMR relaxation times and their dependence with the concentration of the target chemical element.

17. The apparatus of claim 1, wherein the NMR analytics logical circuit is further configured to determine a concentration of a target chemical element in the organ or one or more other internal organs in the subject, based on both the first and second sets of NMR relaxation times and their dependence with the concentration of the target chemical element.

18. The apparatus of claim 1, wherein the NMR analytics logical circuit is further configured to determine the iron concentration in the organ or one or more other internal organs in the subject, based on the proton NMR relaxation times and their dependence with the iron concentration.

19. A computer-implemented method of characterizing a substance in an organ using a unilateral Nuclear Magnetic Resonance ("NMR") probe, the method comprising:
locating the unilateral NMR probe against or in proximity to the subject's body;
generating a static magnetic field that extends into the organ of a subject;
transmitting, using a Radio Frequency ("RF") antenna, one or more RF pulses into the target region;
receiving a first set of NMR signals generated by a first set of atomic nuclei from a first substance as the first set of nuclei realign their spin axes to the magnetic field after being stimulated by the RF pulses;
receiving a second set of NMR signals generated by a second set of atomic nuclei from a second substance as the second set of nuclei realign their spin axes to the magnetic field after being stimulated by the RF pulses;
obtaining the first and second sets of NMR signals, wherein an amplitude of the NMR signals is a measure of proton density;
quantifying and characterizing the first and second substances based on a discrete multi-component analysis of the first and second sets of NMR signals;
wherein the discrete multi-component analysis comprises:
determining first set of NMR relaxation times from the first set of NMR signals;
determining a second set of NMR relaxation times from the second set of NMR signals;
determining a first set of recovery times form the first set of NMR signals;
determining a second set of recovery times from the second set of NMR signals;
determining an independent first diffusion parameter from the first set of NMR signals;
determining an independent second diffusion parameter from the second set of NMR signals;
determining a J-coupling relationship between the first substance and the second substance based on a comparison of the first set of NMR signals and the second set of NMR signals wherein the comparison is based on detected nucleic interaction and resultant electron cloud distortion in the first and second sets of NMR signals caused by application of RF pulse sequences with pulse spacings determined by a time scale characteristic of the J-coupling analysis;
determining whether the first substance is fat based on the discrete multi-component analysis;
determining whether the second substance is fat based on the discrete multi-component analysis;
determining whether the first substance is iron based on the discrete multi-component analysis; and
determining whether the second substance is iron based on the discrete multi-component analysis.

20. The method of claim 19, further comprising measuring selected properties of the organ or other internal organs of the subject by using dedicated pulse sequences to enhance or decimate signals with specific relaxation times.

21. The method of claim 19, wherein determining the J-coupling relationship further comprises using a dedicated fat quantification pulse sequence to discriminate a fat content of the internal organ.

22. The method of claim 19, further comprising quantifying a concentration of the first substance based on a discrete multi-component signal decay analysis of the first and second NMR signals.

23. The method of claim 19, wherein the RF antenna comprises an open coil and is configured to transmit RF pulses in a substantially perpendicular orientation to the static magnetic field.

24. The method of claim 19, wherein the RF antenna comprises an array of sub-antennas and is configured to transmit RF pulses in a substantially perpendicular orientation to the static magnetic field.

25. The method of claim 19, further comprising plotting, on a graphical user interface, a 2-dimensional map of T2 relaxation times and diffusion parameters from the first and second sets of NMR signals, showing the contributions of the first and second substances to the first and second sets of NMR signals.

26. The method of claim 19, further comprising, plotting, on a graphical user interface, a 2-dimensional distribution of T1 recovery times and diffusion parameters from the first and second sets of NMR signals.

27. The method of claim 19, further comprising, determining a fat concentration based on a ratio of the amplitude of the first set of NMR signals as compared with the amplitude of the second set of NMR signals.

28. The method of claim 19, further comprising, obtaining, from a NMR signal database, a calibration signal amplitude for fat in the organ and determining an absolute fat concentration based on a ratio of the amplitude of the first set of NMR signals as compared with the calibration signal.

* * * * *